(12) United States Patent
Coghlan et al.

(10) Patent No.: US 9,737,394 B2
(45) Date of Patent: Aug. 22, 2017

(54) STENT-GRAFT PROSTHESIS FOR PLACEMENT IN THE ABDOMINAL AORTA

(75) Inventors: Kieran Coghlan, Santa Rosa, CA (US); Emilie Simmons, Cotati, CA (US); Meghan Pearson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 755 days.

(21) Appl. No.: 13/458,242

(22) Filed: Apr. 27, 2012

(65) Prior Publication Data
US 2013/0289702 A1    Oct. 31, 2013

(51) Int. Cl.
| | | |
|---|---|---|
| *A61F 2/07* | (2013.01) | |
| *A61F 2/89* | (2013.01) | |
| *A61F 2/06* | (2013.01) | |
| *A61F 2/95* | (2013.01) | |

(52) U.S. Cl.
CPC ......... *A61F 2/07* (2013.01); *A61F 2/89* (2013.01); *A61F 2002/061* (2013.01); *A61F 2002/067* (2013.01); *A61F 2002/9511* (2013.01); *A61F 2250/0018* (2013.01); *A61F 2250/0029* (2013.01)

(58) Field of Classification Search
USPC .............................. 623/1.13, 1.16, 1.35, 1.32
See application file for complete search history.

(56) References Cited

U.S. PATENT DOCUMENTS

| | | |
|---|---|---|
| 5,425,765 A | 6/1995 | Tiefenbrun et al. |
| 5,617,878 A | 4/1997 | Taheri |
| 5,782,904 A | 7/1998 | White et al. |
| 6,042,605 A | 3/2000 | Martin et al. |
| 6,352,553 B1 | 3/2002 | Van der Burg et al. |

(Continued)

FOREIGN PATENT DOCUMENTS

| | | |
|---|---|---|
| EP | 2298248 | 3/2011 |
| JP | 2001-231868 | 8/2001 |

(Continued)

OTHER PUBLICATIONS

Bungay et al. "Initial Experience With a New Fenestrated Stent Graft" Journal of Vascular Surgery, 2011, pp. 1-7.

(Continued)

*Primary Examiner* — David Isabella
*Assistant Examiner* — Leslie Lopez

(57) ABSTRACT

A self-expanding main vessel stent-graft includes a trunk portion configured for placement within the abdominal aorta and a bifurcated portion configured for placement above the aortic bifurcation of the common iliac arteries. The trunk portion includes a proximal end section having an anchor stent and a seal stent that accommodates a scallop or open-top fenestration; a suprarenal body section having at least one stent of variable stiffness to accommodate branch vessel prosthesis deployed alongside the main vessel stent-graft; a branch connection section having opposing couplings for connecting the main vessel stent-graft to branch vessel prostheses deployed within the renal arteries; an infrarenal body section having at least one stent of uniform stiffness; and a transition section for transitioning into the bifurcated portion. The main vessel stent-graft is configured to treat short-neck infrarenal, juxtarenal, and/or suprarenal aneurysms in a wide range of patient anatomies.

20 Claims, 23 Drawing Sheets

(56) References Cited

U.S. PATENT DOCUMENTS

| | | | |
|---|---|---|---|
| 6,352,561 B1 | 3/2002 | Leopold et al. | |
| 6,361,637 B2 | 3/2002 | Martin et al. | |
| 6,471,722 B1 | 10/2002 | Inoue | |
| 6,520,986 B2 | 2/2003 | Martin et al. | |
| 6,524,335 B1* | 2/2003 | Hartley et al. | 623/1.13 |
| 6,551,350 B1 | 4/2003 | Thornton et al. | |
| 7,131,991 B2 | 11/2006 | Zarins et al. | |
| 7,306,623 B2 | 12/2007 | Watson | |
| 7,413,573 B2* | 8/2008 | Hartley et al. | 623/1.13 |
| 7,438,721 B2 | 10/2008 | Doig et al. | |
| 7,537,606 B2 | 5/2009 | Hartley et al. | |
| 7,678,141 B2 | 3/2010 | Greenan et al. | |
| 7,682,380 B2 | 3/2010 | Thornton et al. | |
| 7,736,571 B2 | 6/2010 | Trapp | |
| 7,867,270 B2 | 1/2011 | Hartley et al. | |
| 7,955,374 B2 | 6/2011 | Erickson et al. | |
| 2003/0125802 A1* | 7/2003 | Callol et al. | 623/1.35 |
| 2003/0199967 A1* | 10/2003 | Hartley et al. | 623/1.13 |
| 2007/0032852 A1 | 2/2007 | Machek et al. | |
| 2007/0055360 A1 | 3/2007 | Hanson et al. | |
| 2007/0208256 A1 | 9/2007 | Marilla | |
| 2007/0225797 A1 | 9/2007 | Krivoruchko | |
| 2007/0233220 A1 | 10/2007 | Greenan | |
| 2007/0244547 A1 | 10/2007 | Greenan | |
| 2007/0250152 A1 | 10/2007 | Xiao et al. | |
| 2008/0294234 A1 | 11/2008 | Hartley et al. | |
| 2009/0204202 A1 | 8/2009 | Dierking et al. | |
| 2011/0118816 A1 | 5/2011 | Jensen et al. | |
| 2011/0125244 A1 | 5/2011 | Roeder et al. | |
| 2011/0125249 A1 | 5/2011 | Jensen et al. | |
| 2011/0190868 A1 | 8/2011 | Ducke et al. | |
| 2011/0208289 A1 | 8/2011 | Shalev | |
| 2011/0270380 A1 | 11/2011 | Bruszewski | |
| 2012/0035714 A1 | 2/2012 | Ducke et al. | |
| 2012/0046728 A1 | 2/2012 | Huser et al. | |

FOREIGN PATENT DOCUMENTS

| | | |
|---|---|---|
| WO | WO01/00112 | 1/2001 |
| WO | WO2006/113501 | 10/2006 |
| WO | WO2010/024879 | 3/2010 |

OTHER PUBLICATIONS

PCT/US2013/026680, International Search Report and the Written Opinion of the International Searching Authority, dated Jun. 25, 2013.

* cited by examiner

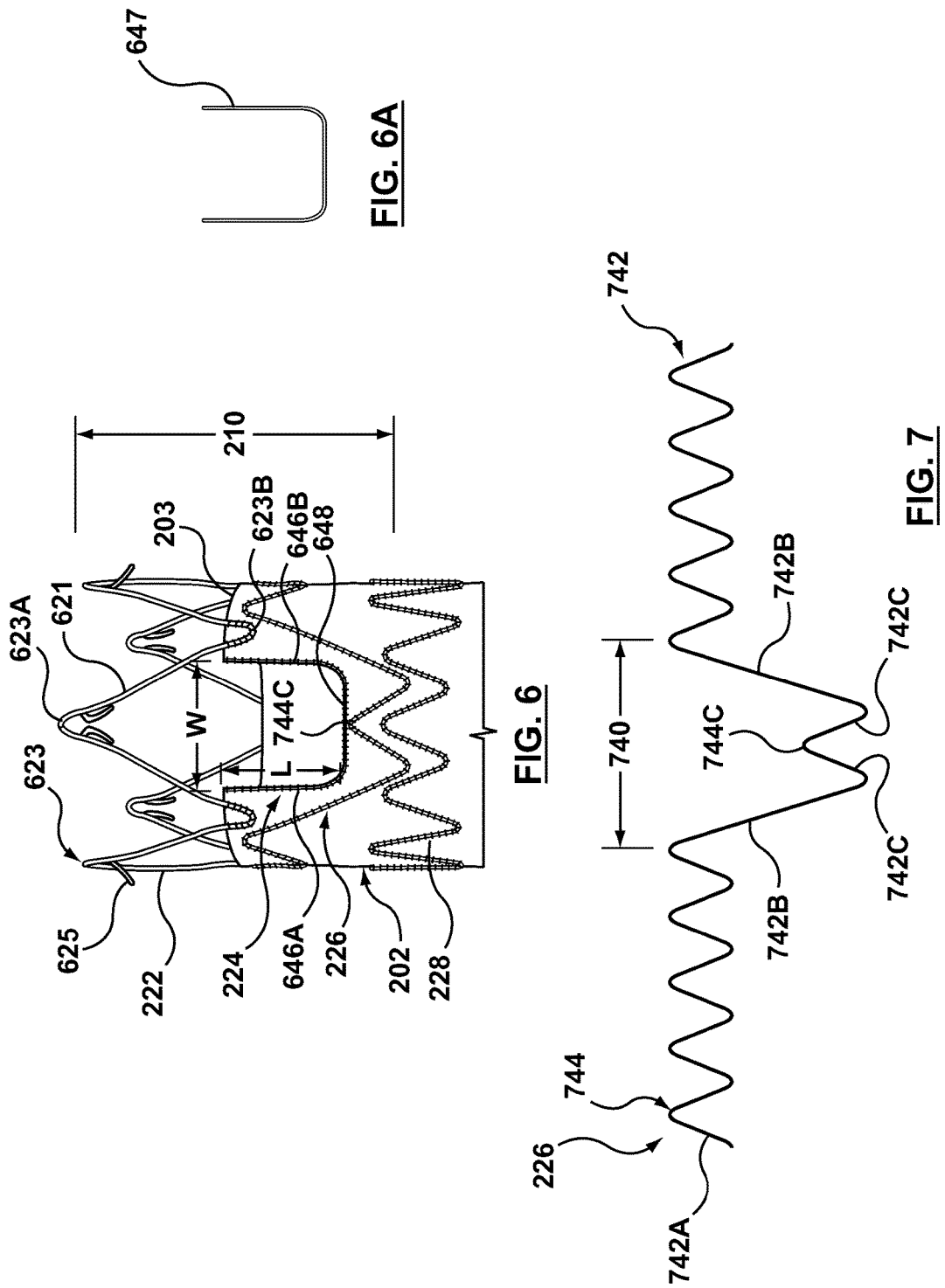

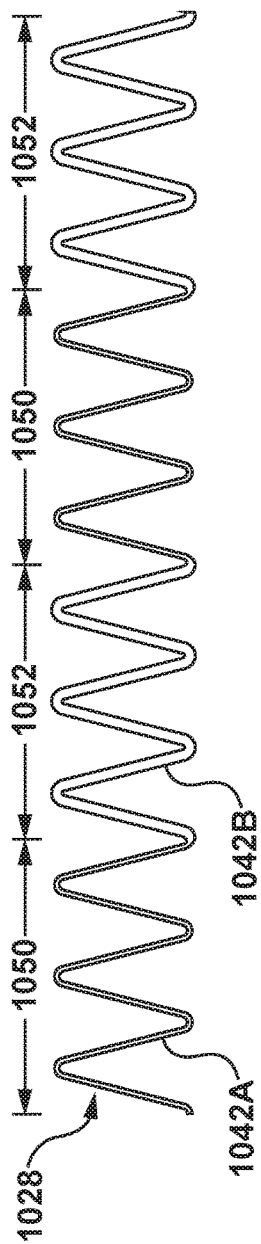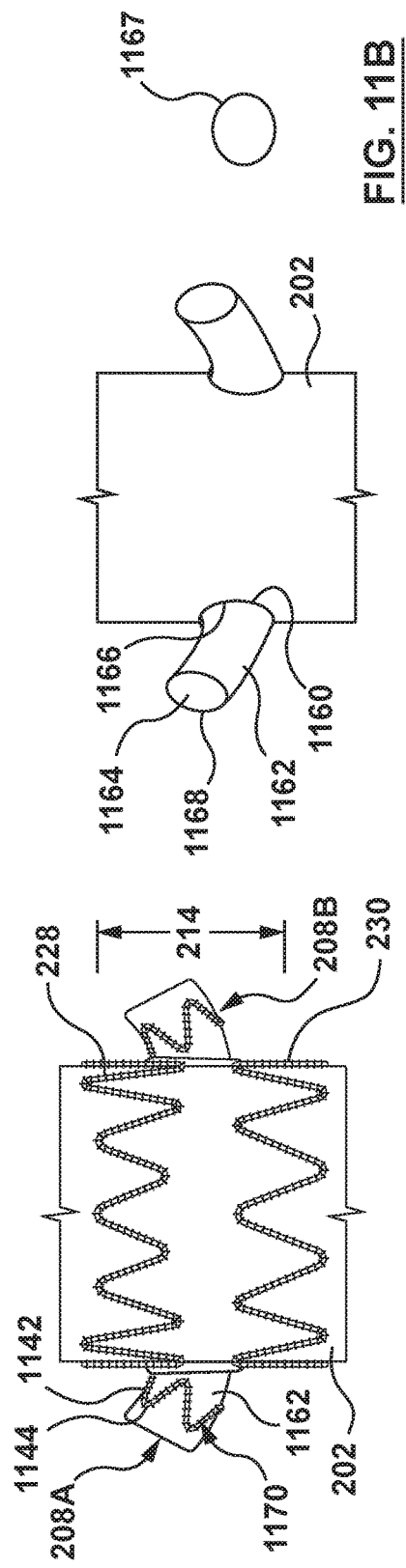

STENT-GRAFT PROSTHESIS FOR PLACEMENT IN THE ABDOMINAL AORTA

FIELD OF THE INVENTION

This invention relates generally to endoluminal medical devices and procedures, and more particularly to an endoluminal prosthesis or graft configured for placement in the abdominal aorta having branch vessels extending therefrom.

BACKGROUND OF THE INVENTION

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Abdominal aortic aneurysms include aneurysms present in the aorta distal to the diaphragm, e.g., pararenal aorta and the branch arteries that emanate therefrom, including the renal arteries and the superior mesenteric artery (SMA). Abdominal aortic aneurysms are bulges or weakening regions in the aortic wall and are frequently classified by their location relative to the renal arteries. Referring to FIGS. 1A-1C, various types of abdominal aortic aneurysms are shown for illustrative purposes. In FIGS. 1A-1C, a portion of an aorta A is shown extending down to the aortic bifurcation in which aorta A bifurcates into the common iliac arteries, including a right iliac artery RI and a left iliac artery LI. A right renal artery RRA and a left renal artery LRA extend from aorta A, as does the superior mesenteric artery (SMA) which arises from the anterior surface of the abdominal aorta. In FIG. 1A, an infrarenal abdominal aortic aneurysm $AAA_I$ is located distal to the renal arteries. In FIG. 1B, a juxtarenal abdominal aortic aneurysm $AAA_J$ approaches or extends up to, but does not involve, the renal arteries. In FIG. 1C, a suprarenal abdominal aortic aneurysm $AAA_S$ involves and extends above the renal arteries.

In some cases, the aneurysmal region of the aorta can be bypassed by use of an endoluminally delivered tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without challenges. In particular, care must be taken so that critical branch arteries are not covered or occluded by the stent-graft, yet the stent-graft must seal against the aorta wall and provide a flow prosthesis for blood to flow past the aneurysmal site. Where the aneurysm is located immediately adjacent to the branch arteries, there is a need to deploy the stent-graft in a location which partially or fully extends across the location of the origin of the branch arteries from the aorta to ensure sealing of the stent-graft to the artery wall.

To accommodate side branches, main vessel stent-grafts having a fenestration or opening in a side wall thereof may be utilized. The main vessel stent-graft is positioned to align its fenestration with the ostium of the branch vessel. In use, a proximal end of the stent-graft, having one or more side openings, is prepositioned and securely anchored in place so that its fenestrations or openings are oriented when deployed to avoid blocking or restricting blood flow into the side branches. Fenestrations by themselves do not form a tight seal or include discrete prosthesis(s) through which blood can be channeled into the adjacent side branch artery. As a result, blood leakage is prone to occur into the space between the outer surface of the main aortic stent-graft and the surrounding aortic wall between the edge of the graft material surrounding the fenestrations and the adjacent vessel wall. Similar blood leakage can result from post-implantation migration or movement of the stent-graft causing misalignment between the fenestration(s) and the branch artery(ies), which may also result in impaired flow into the branch artery(ies).

In some cases, the main vessel stent-graft is supplemented by another stent-graft, often referred to as a branch vessel stent-graft or branch vessel stent-graft. The branch vessel stent-graft is deployed through the fenestration into the branch vessel to provide a prosthesis for blood flow into the branch vessel. The branch vessel stent-graft is preferably sealingly connected to the main vessel stent-graft in situ to prevent undesired leakage between it and the main vessel stent-graft. This connection between the branch vessel stent-graft and main vessel stent-graft may be difficult to create effectively in situ and is a site for potential leakage.

Particular issues arise in treating juxtarenal abdominal aortic aneurysms, as shown in FIG. 1B, and suprarenal abdominal aortic aneurysms, shown in FIG. 1C. Similar issues arise in treating so-called short-neck infrarenal aneurysms, in which only a small length (i.e., less than 10 mm) of non-aneurysed tissue is present between the renal arteries and the proximal end of the infrarenal aneurysm. Often, a proximal infrarenal neck or non-aneurysmal tissue of 10-15 mm length is usually required to allow endovascular repair of abdominal aortic aneurysms (EVAR). Since juxtarenal and suprarenal aneurysms extend up to or above the renal arteries, there is an insufficient non-aneurysmal length or neck of the aorta distally of (i.e., distal to or downstream of) the renal arteries for a stent-graft to deploy and seal against the vessel wall. Accordingly, it is necessary to deploy some of the stent-graft proximally of (i.e., above or upstream of) the renal arteries, which requires consideration of the superior mesenteric artery (SMA) and not to occlude or block blood flow thereto. Due to variations in patient anatomy, short-neck infrarenal, juxtarenal, and suprarenal aneurysms are typically treated with open repair or a custom designed, fenestrated endovascular stent-graft. Custom designed stent-grafts require a significant lead time, i.e., 6-8 weeks, and are costly to design and manufacture.

Thus, there remains a need in the art for improvements in stent-graft structures for treating abdominal aortic aneurysms that require directing flow from the aorta into branch vessels emanating therefrom, such as the renal arteries and the superior mesenteric artery (SMA).

BRIEF SUMMARY OF THE INVENTION

Embodiments hereof relate to a self-expanding main vessel stent-graft configured for placement in the abdominal aorta. The main vessel stent-graft includes a trunk portion configured for placement within the abdominal aorta and a bifurcated portion configured for placement within the common iliac arteries. The trunk portion includes a proximal end section having an anchor stent and a seal stent that accommodates a scallop or open-top fenestration; a suprarenal body section having at least one stent of variable stiffness to accommodate a branch vessel prosthesis deployed alongside the main vessel stent-graft; a branch connection section having opposing couplings for connecting the main vessel stent-graft to branch vessel prostheses deployed within the renal arteries; an infrarenal body section having at least one stent of uniform stiffness; and a transition section for transitioning into the bifurcated portion.

Embodiments hereof also relate to a prosthesis for implantation within a blood vessel which includes a tubular body of a graft material, first and second opposing couplings that extend outwardly from the tubular body, and a variable stiffness stent coupled to the tubular body proximal of the couplings. Each coupling includes a base coupled to the tubular body, a top spaced from the tubular body, and a coupling lumen disposed between the base and the top that is in fluid communication with a lumen defined by the tubular body. The variable stiffness stent includes a plurality of crowns and a plurality of struts with each crown being formed between a pair of opposing struts, and includes at least two zones of relatively greater flexibility that are approximately circumferentially aligned with the couplings.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 illustrates an enlarged or zoomed-in view of a proximal end section of the main vessel stent-graft of FIG. 2.

FIG. 6A illustrates a radiopaque U-shaped wire that may be disposed around a scallop of the proximal end section of FIG. 6.

FIG. 7 illustrates a seal stent of the proximal end section of FIG. 6, wherein the seal stent is laid out flat for illustrative purposes.

FIG. 10 illustrates another embodiment of a variable stiffness body stent, wherein the variable stiffness body stent is laid out flat for illustrative purposes.

FIG. 11 illustrates an enlarged or zoomed-in view of a branch connection section of the main vessel stent-graft of FIG. 2, while FIG. 11A also illustrates the branch connection section of the main vessel stent-graft with stents removed for illustrative purposes.

FIG. 11B illustrates a wire ring that may be disposed around a top of couplings of the branch connection section of FIG. 11.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used herein with reference to the direction of blood flow from the heart in using the stent-graft system in the vasculature: "distal" indicates an apparatus portion distant from, or a direction away from the heart and "proximal" indicates an apparatus portion near to, or a direction towards to the heart. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a super-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as aorta, the invention may also be used in any other blood vessels and body passageways where it is deemed useful. Furthermore, there is no intention to be bound by any expressed or implied theory presented in the preceding technical field, background, brief summary or the following detailed description.

Figure 1A:
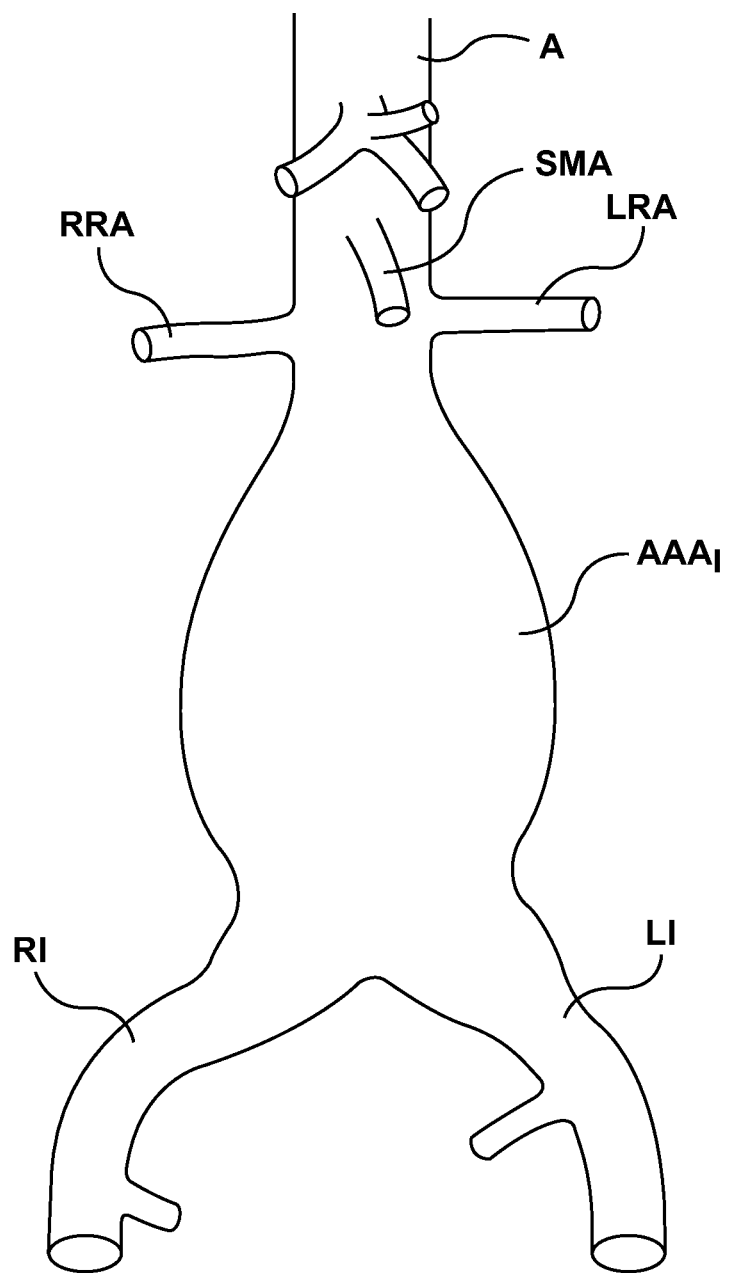
FIGS. 1A-1C are schematic illustrations of various types of abdominal aortic aneurysms.
Figure 1B:
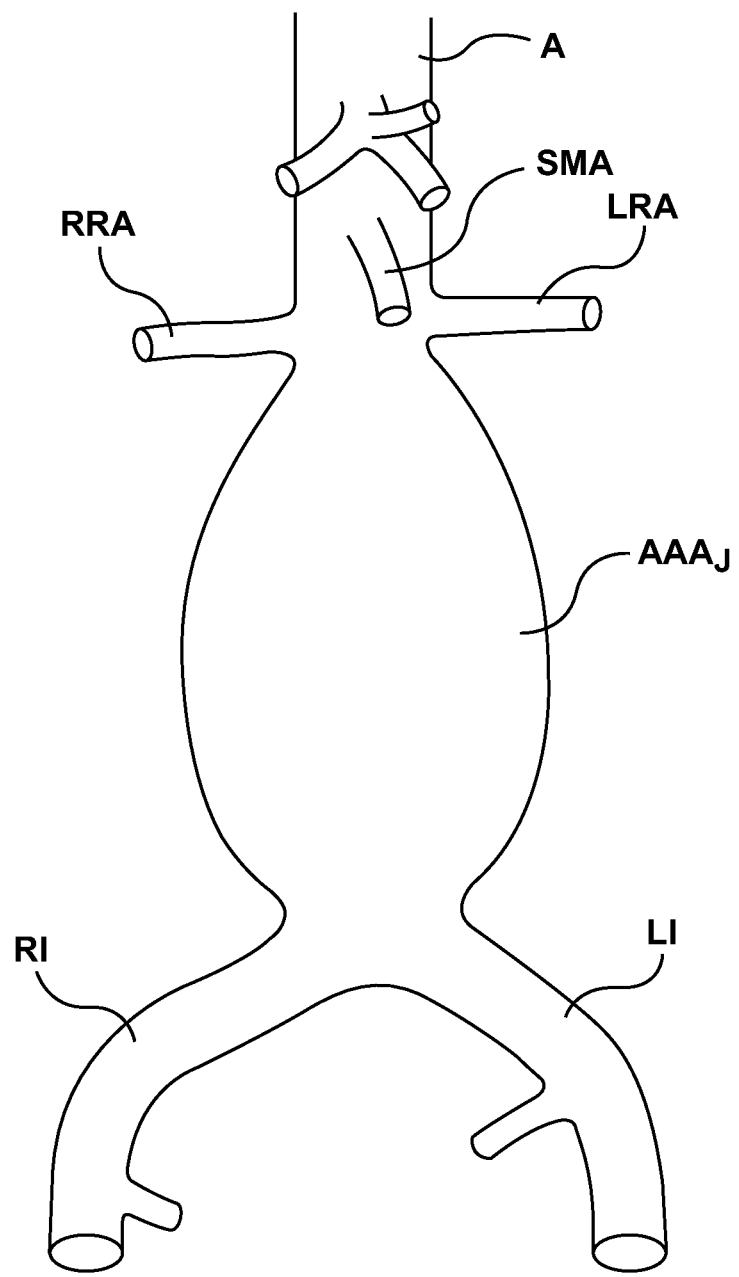
Figure 1C:
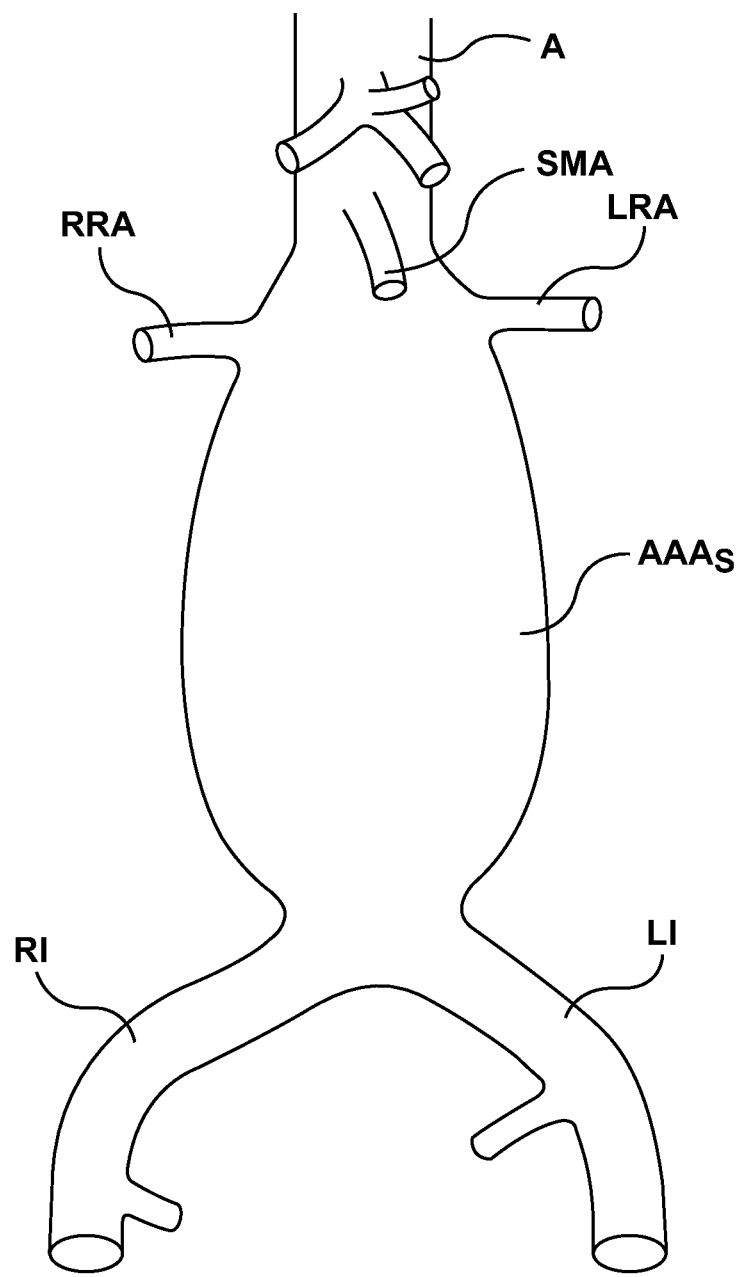
Figure 2:
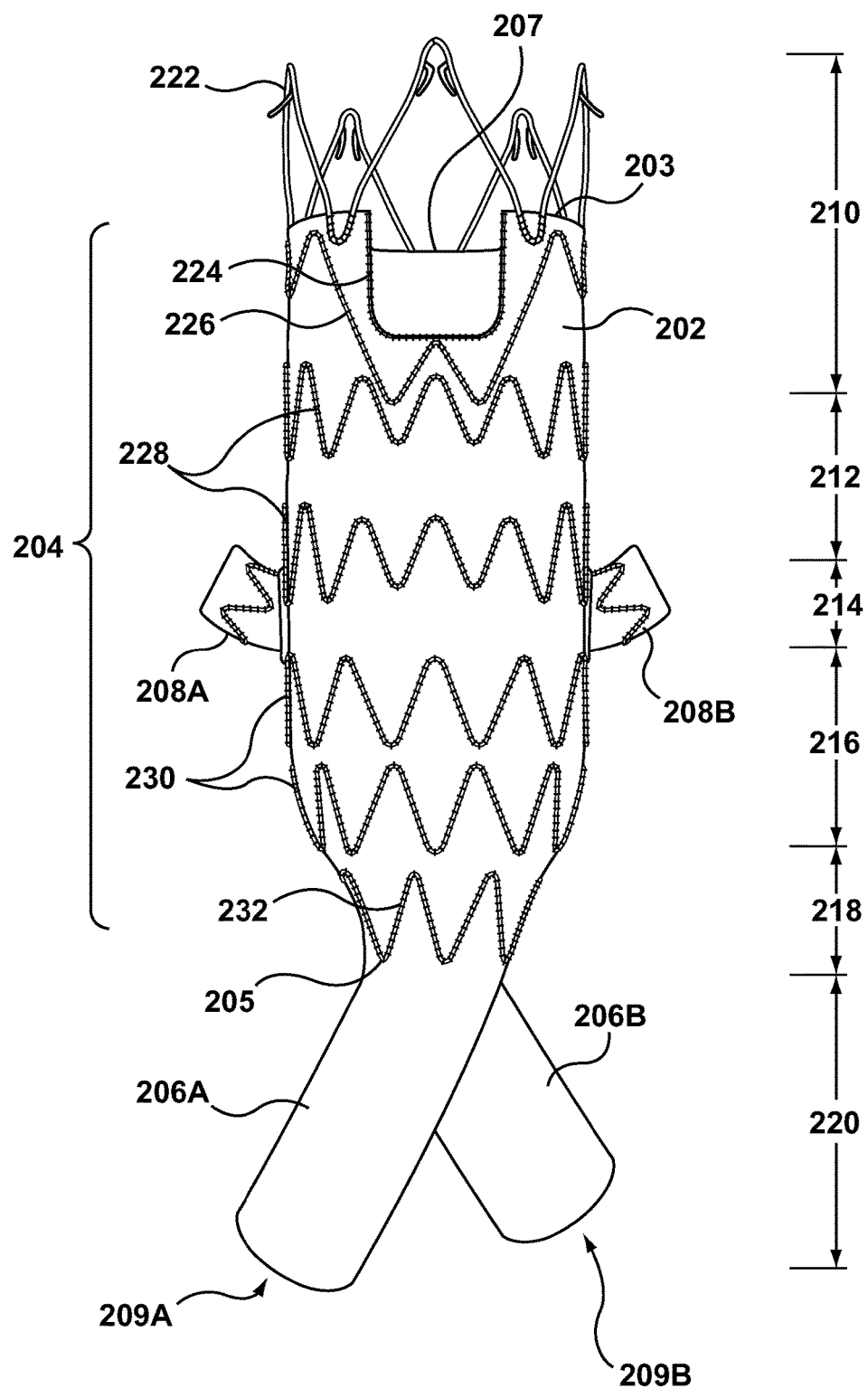
FIG. 2 is a side view of a main vessel stent-graft according to an embodiment hereof, wherein the main vessel stent-graft is in an expanded or deployed state.
Figure 4:
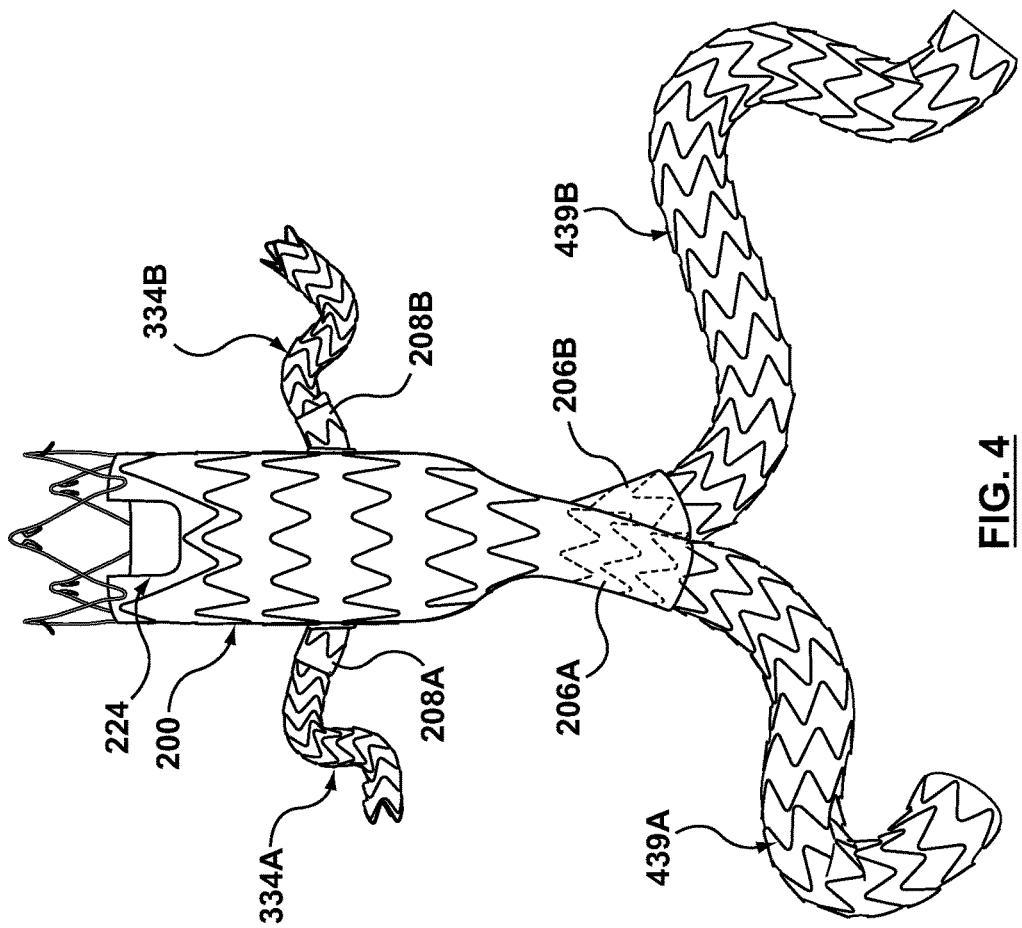
FIG. 4 is a perspective view of the main vessel stent-graft of FIG. 2 having two branch vessel stent-grafts of FIG. 3 extending therefrom.
Figure 3:
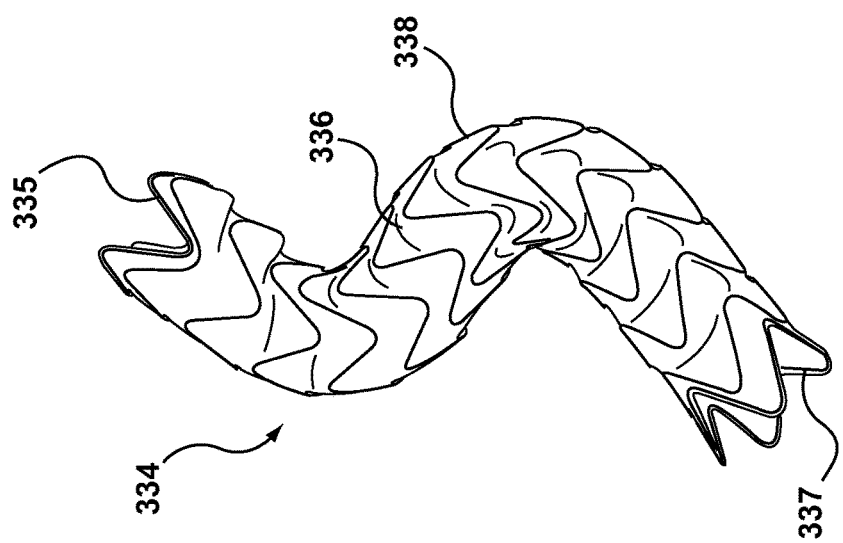
FIG. 3 is a perspective view of a branch vessel stent-graft according to an embodiment hereof, wherein the branch vessel stent-graft is in an expanded or deployed state.
Figure 5:
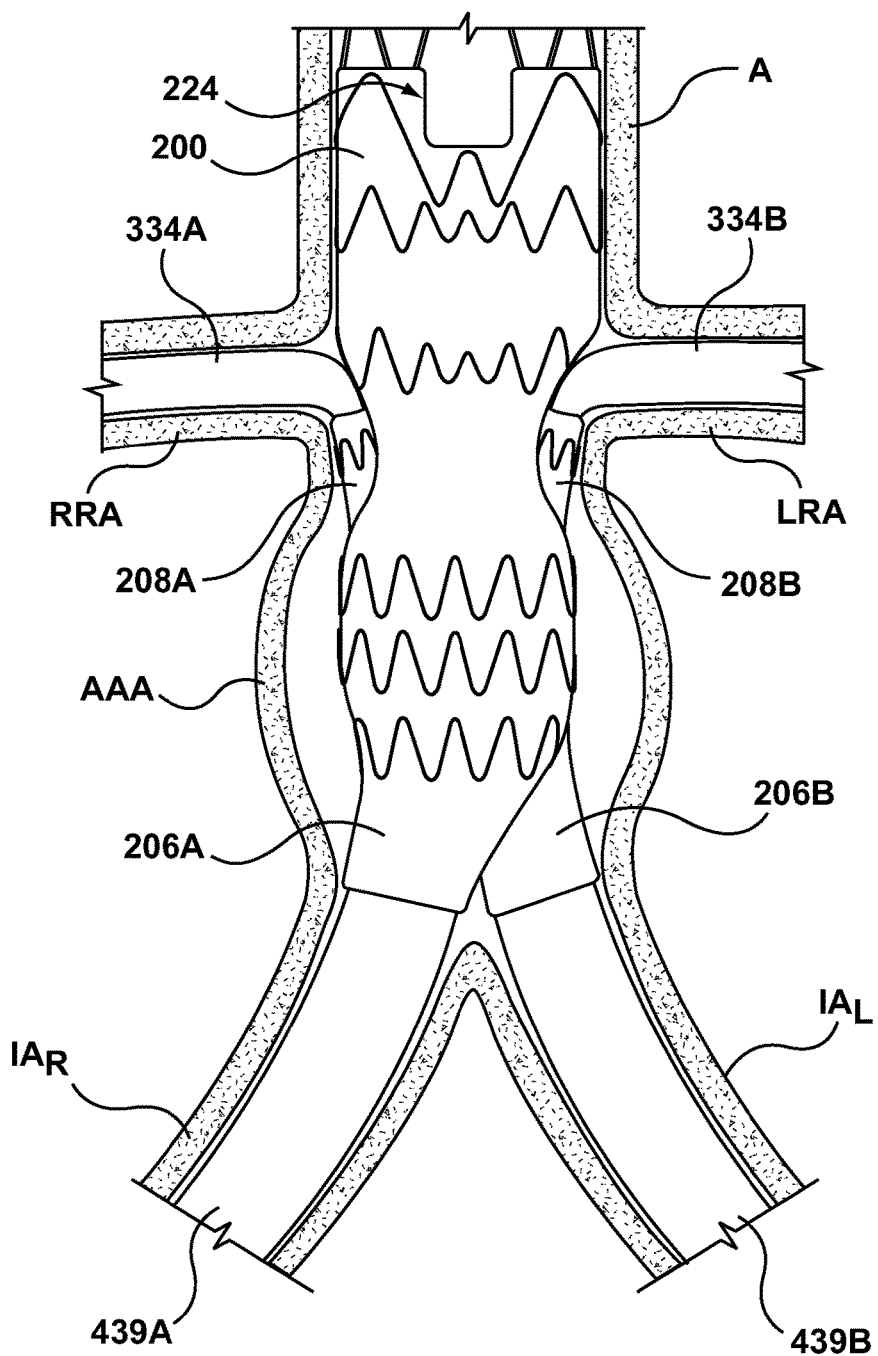
FIG. 5 is a sectional view of the main vessel stent-graft of FIG. 2 having two branch vessel stent-grafts of FIG. 3 extending therefrom deployed in situ.

With reference to FIGS. 2-5, a self-expanding main vessel stent-graft prosthesis 200 is configured for placement in a vessel such as the abdominal aorta. Main vessel stent-graft 200 is an off-the-shelf device, i.e., is not a device custom designed for a particular patient's anatomy, that is configured to treat short-neck infrarenal, juxtarenal, and/or suprarenal aneurysms in a wide range of patient anatomies. FIG. 2 illustrates a side view of main vessel stent-graft 200 in its deployed or expanded state or configuration, FIG. 3 illustrates a perspective view of an exemplary branch vessel stent-graft 334 in its deployed or expanded state or configuration, and FIG. 4 illustrates a perspective view of main vessel stent-graft 200 having branch vessel stent-grafts 334A, 334B and limb stent-grafts 439A, 439B extending from main vessel stent-graft 200. FIG. 5 illustrates a cross-sectional view of main vessel stent-graft 200 deployed in an abdominal aorta having an abdominal aortic aneurysm AAA, with branch vessel stent-grafts 334A, 334B extending from main vessel stent-graft 200 and extending into the renal arteries and limb stent-grafts 439A, 439B extending into the common iliac arteries.

With reference to FIG. 2, main vessel stent-graft 200 includes a first or trunk portion 204 and a second or bifurcated portion 220. In an embodiment, bifurcated portion 220 is integrally formed with trunk portion 204 as a single or unitary prosthesis. In another embodiment, bifurcated portion 220 may be formed separately from trunk portion 204 and coupled thereto. As shown in FIG. 5, when deployed in situ, trunk portion 204 is configured for placement within the abdominal aorta and bifurcated portion 220 is configured for placement proximal to or above the aortic bifurcation of the right and left common iliac arteries.

Trunk portion 204 includes a generally tubular or cylindrical body 202 that defines a lumen 207 and has a first edge or end 203 and a second edge or end 205. Tubular body 202 may be formed from any suitable graft material, for example and not limited to, a low-porosity woven or knit polyester, DACRON material, expanded polytetrafluoroethylene, polyurethane, silicone, ultra high molecular weight polyethylene, or other suitable materials. In another embodiment, the graft material could also be a natural material such as pericardium or another membranous tissue such as intestinal submucosa.

Bifurcated portion 220 extends from second end 205 of tubular body 202, and includes a first tubular leg or extension 206A and a second tubular leg or extension 206B. Legs 206A, 206B define lumens 209A, 209B, respectively, that are in fluid communication with lumen 207 of tubular body 202. In an embodiment in which bifurcated portion 220 is integrally formed with trunk portion 204 as a single or unitary prosthesis, legs 206A, 206B are integrally formed with tubular body 202 and thus are formed from the same graft material as tubular body 202. In another embodiment in which bifurcated portion 220 is formed separately from trunk portion 204 and coupled thereto, legs 206A, 206B may be formed from the same graft material or a different graft material than tubular body 202. In the embodiment shown, legs 206A, 206B are of equal length and are oriented anterior and posterior within the abdominal aorta when deployed in the abdominal aorta. As will be described in more detail herein with respect to FIG. 27, orienting legs 206A, 206B anterior and posterior within the abdominal aorta facilitates cannulation of the contralateral leg while also providing flexibility in the selection of the percutaneous entry site to allow introduction of the delivery system through the left or right femoral artery.

Referring now to FIG. 3, main vessel stent-graft 200 is to be utilized with one or more branch vessel stent-grafts 334 that direct blood flow and perfuse branch vessels that emulate from the abdominal aorta. Branch vessel stent-graft 334 includes a generally tubular or cylindrical body 336 that defines a lumen (not shown) and has a first edge or end 335 and a second edge or end 337. Tubular body 336 may be formed from any suitable graft material, for example and not limited to, expanded polytetrafluoroethylene, a low-porosity woven or knit polyester, DACRON material, polyurethane, silicone, ultra high molecular weight polyethylene, or other suitable materials. Branch vessel stent-graft 334 also includes at least one radially-compressible stent or scaffold 338 that is coupled to tubular body 336 for supporting the graft material and that is operable to self-expand into apposition with an interior wall of a body vessel (not shown). Stent 338 is constructed from a self-expanding or spring material, such as nitinol, and has sufficient radial spring force and flexibility to conformingly engage branch vessel stent-graft 334 with the blood vessel inner wall, to avoid excessive leakage, and prevent pressurization of the aneurysm, i.e., to provide a leak-resistant seal. Ends 335, 337 of tubular body 336 may be scalloped such that the graft material generally follows the shape of the stents adjacent to ends 335, 337, thereby preventing excess graft material from folding, kinking, or bunching. It will be apparent to one of ordinary skill in the art that branch vessel stent-graft 334 is merely exemplary; main vessel stent-graft 200 may be utilized with branch vessel stent-grafts of various other configurations including but not limited to balloon-expandable stent-grafts.

With reference to the perspective view of FIG. 4 and the cross-sectional view of main vessel stent-graft 200 deployed in situ of FIG. 5, branch vessel stent-grafts 334A, 334B are delivered and deployed within couplings 208A, 208B of main vessel stent-graft 200, extending into right renal artery RRA and left renal artery LRA, respectively. The incremental delivery method and corresponding staged release of main vessel stent-graft 200 is described in detail herein with respect to FIGS. 13-25. In addition to branch vessel stent-grafts 334A, 334B, limb stent-grafts 439A, 439B may be delivered and deployed within legs 206A, 206B of main vessel stent-graft 200, extending into right iliac artery $IA_R$ and left iliac artery $IA_L$, respectively. Limb stent-grafts 439A, 439B are configured to be deployed within the common iliac arteries, and generally include a tubular body of graft material having at least one radially-compressible stent or scaffold coupled thereto as described above with respect to branch vessel stent-grafts 334A, 334B.

For illustrative purposes, tubular body 202 of main vessel stent-graft is described herein as having five integral portions or sections. More particularly, referring back to FIG. 2, tubular body 202 includes (1) a proximal end section 210 having an anchor stent 222 and a seal stent 226 that accommodates a scallop 224 cut out or removed from tubular body 202; (2) a suprarenal body section 212 having at least one stent or scaffold 228 of variable stiffness; (3) a branch connection section 214 having opposing couplings 208A, 208B for connecting stent-graft prosthesis 200 to branch vessel prostheses 334A, 334B (shown in FIGS. 3-5) to accommodate the right and left renal arteries, respectively; (4) an infrarenal body section 216 having at least one stent or scaffold 230 of uniform stiffness; and (5) a transition or distal end section 218 having at least one stent or scaffold 232 for transitioning into bifurcated portion 220. Each portion of tubular body 202 is described in more detail herein.

FIG. 6 illustrates an enlarged or zoomed-in view of proximal end section 210 of tubular body 202. Proximal end section 210 includes anchor stent 222, which is a radially-compressible ring or scaffold that is operable to self-expand into apposition with an interior wall of a body vessel (not shown). Anchor stent 222 is constructed from a self-expanding or spring material, such as nitinol, and is a sinusoidal patterned ring including a plurality of crowns or bends 623 and a plurality of struts or straight segments 621 with each crown being formed between a pair of opposing struts. In an embodiment, anchor stent 222 is a laser-cut stent and the resulting struts and bends 621, 623 have a rectangular cross-section or approximately a rectangular cross-section. In another embodiment, anchor stent 222 may be formed from a single, continuous wire that may be solid or hollow and have a circular cross-section. In another embodiment, the cross-section of the wire that forms anchor stent 222 may be an oval, square, rectangular, or any other suitable shape. Anchor stent 222 is coupled to the graft material so as to have a first or proximal-most set of crowns 623A that extend outside of or beyond first edge 203 of tubular body 202 in an open web or free-flow configuration and a second or opposing set of crowns 623B that is coupled to first edge 203 of tubular body 202. Crowns 623B are coupled to tubular body 202 by stitches or other means known to those of skill in the art. In the embodiment shown in FIG. 6, crowns 623B are coupled to an outside surface of tubular body 202. However, crowns 623B may alternatively be coupled to an inside surface of tubular body 202. Unattached or free crowns 623A may include barbs 625 for embedding into and anchoring into vascular tissue when stent-graft prosthesis 200 is deployed in situ. In an embodiment, anchor stent 222 is the ENDURANT® II suprarenal stent, manufactured by Medtronic, Inc., of Minneapolis, Minn.

Proximal end section 210 of tubular body 202 also includes scallop 224 cut out or removed from the graft material of tubular body 202. Scallop 224 is an open-topped fenestration. When deployed in situ, scallop 224 is positioned within the aorta distal of the superior mesenteric artery (SMA) and extends around and/or frames the ostium of the SMA. In short-neck infrarenal, juxtarenal, and/or suprarenal aneurysms, first edge 203 of tubular body 202 is deployed within the abdominal aorta at or near the superior mesenteric artery (SMA). In order to avoid blockage of blood flow into the superior mesenteric artery (SMA), stent-graft prosthesis 200 is positioned or oriented within the abdominal aorta such that scallop 224 is positioned around the ostium of the superior mesenteric artery (SMA) and the graft material of tubular body 202 does not occlude the ostium of the SMA. The presence of scallop 224 for the SMA allows for main vessel stent-graft 200 to deploy and seal against a sufficient length, i.e., greater than 10 mm, of healthy or non-aneurysmal tissue distal to the SMA for patients suffering from short-neck infrarenal, juxtarenal, and/or suprarenal aneurysms.

Scallop 224 may have a generally rectangular or oblong shape having two generally straight opposing side edges 646A, 646B with a generally straight bottom edge 648 extending there between as shown in FIG. 6, with a width W of edge 648 ranging between 8-12 mm and a length L of edges 646A, 646B ranging between 8-12 mm. In an embodiment, scallop 224 has a width 224 of 12 mm and a length L of 10 mm. As will be understood by those of ordinary skill in the art, "side" and "bottom" are relative terms and utilized herein for illustration purposes only. Further, it will be understood by one of ordinary skill in the art that the shape or configuration of scallop 224 may vary as long as it accommodates the superior mesenteric artery (SMA). For example, the straight opposing side edges may be slanted or angled away from each other or may be parallel to each other, the side edges and/or the bottom edge may be curved, or the corners of scallop 224 may be rounded to give scallop 224 a U-shaped configuration. In an embodiment shown in FIG. 6A, a U-shaped wire 647 may be disposed around the edges of the scallop, for example by folding graft material over the wire and stitching the folded over portion of the graft material to itself. In one embodiment, wire 647 is formed from a radiopaque material in order to aid in positioning scallop 224 around the SMA. A suitable radiopaque material includes any relatively heavy metal which is generally visible by X-ray fluoroscopy such as tantalum, titanium, platinum, gold, silver, palladium, iridium, and the like.

Proximal end section 210 of tubular body 202 also includes seal stent 226, which is configured to accommodate scallop 224 and maximize patient applicability as will be described in more detail herein. Seal stent 226 is a radially-compressible ring or scaffold that is coupled to tubular body 202 for supporting the graft material and is operable to self-expand into apposition with an interior wall of a body vessel (not shown). Seal stent 226 is constructed from a self-expanding or spring material, such as nitinol, and is a sinusoidal patterned ring including a plurality of crowns or bends 744 and a plurality of struts or straight segments 742 with each crown being formed between a pair of opposing struts. Seal stent 226 may be formed from a single, continuous wire that may be solid or hollow and have a circular cross-section. In an embodiment, the wire that forms seal stent 226 has a diameter between 0.011-0.014 inches. In another embodiment, the cross-section of the wire that forms seal stent 226 may be an oval, square, rectangular, or any other suitable shape. Seal stent 226 is coupled to tubular body 202, proximal of and adjacent to first end 203 thereof and anchor stent 222, and is covered or lined by the graft material of tubular body 202. Seal stent 226 is coupled to tubular body 202 by stitches or other means known to those of skill in the art. In the embodiment shown in FIG. 6, seal stent 226 is coupled to an outside surface of tubular body 202. However, seal stent 226 may alternatively be coupled to an inside surface of tubular body 202. When stent-graft prosthesis 200 is used for treating an aneurysm, seal stent 226 has sufficient radial spring force and flexibility to conformingly engage proximal end section 210 of tubular body 202 with the blood vessel inner wall, to avoid excessive leakage, and prevent pressurization of the aneurysm, i.e., to provide a leak-resistant seal. Although some leakage of blood or other body fluid may occur into the aneurysm isolated by stent-graft prosthesis 200, an optimal seal will reduce the chances of aneurysm pressurization and resulting rupture.

In order to accommodate scallop 224 cut out of the graft material of tubular body 202, the length of struts or straight segments 742 of seal stent 226 are not uniform. Rather, seal stent 226 includes an integral elongated portion 740 in which at least two of the struts 742B are lengthened or elongated with respect to struts 742A, which make up the remaining struts of seal stent 226 except for integral elongated portion 740, to create a seal around scallop 224 in the graft material. As shown in FIG. 7, which illustrates seal stent 226 laid flat out for illustrative purposes, elongated portion 740 has a long-short-short-long strut configuration or pattern. More particularly, elongated portion 740 includes four consecutive struts, a first relatively long strut 742B, two consecutive relatively short struts 742C, and a second relatively long strut 742B. In one embodiment, short struts 742C are approximately the same length as struts 742A of seal stent 226, although short struts 742C may be shorter or longer than struts 742A. In the embodiment shown, struts 742A are each of the same length. In another embodiment hereof (not shown), struts 742A may be variable or different lengths. The longer length of long struts 742B is greater than the length L of scallop 224 and the length of a single short strut 742C. In an embodiment, the length of long struts 742B may range between 10-12 mm and the length of struts 742A and struts 742C may range between 4-8 mm. Elongated portion 740 of seal stent 226 is positioned around scallop 224 of tubular body 202, with long struts 742B extending alongside or flanking opposing side edges 646A, 646B of scallop 224 and short struts 742C extending distal to or under bottom edge 648. Crown 744C, which extends between the two consecutive relatively short struts 742C, is coupled to tubular body 202 slightly distal to or under bottom edge 648 of scallop 224. In one embodiment, crown 744C is positioned at the mid-point or middle of bottom edge 648. Elongated portion 740 allows seal stent 226 to conformingly engage and seal the edges of scallop 224 with the blood vessel inner wall. Due to the configuration of seal stent 226, stent-graft prosthesis 200 may include scallop 224 in the traditional proximal seal zone of the stent-graft and thereby accommodate the superior mesenteric artery (SMA) while maintaining seal integrity.

Figures 8, 8A, 9:
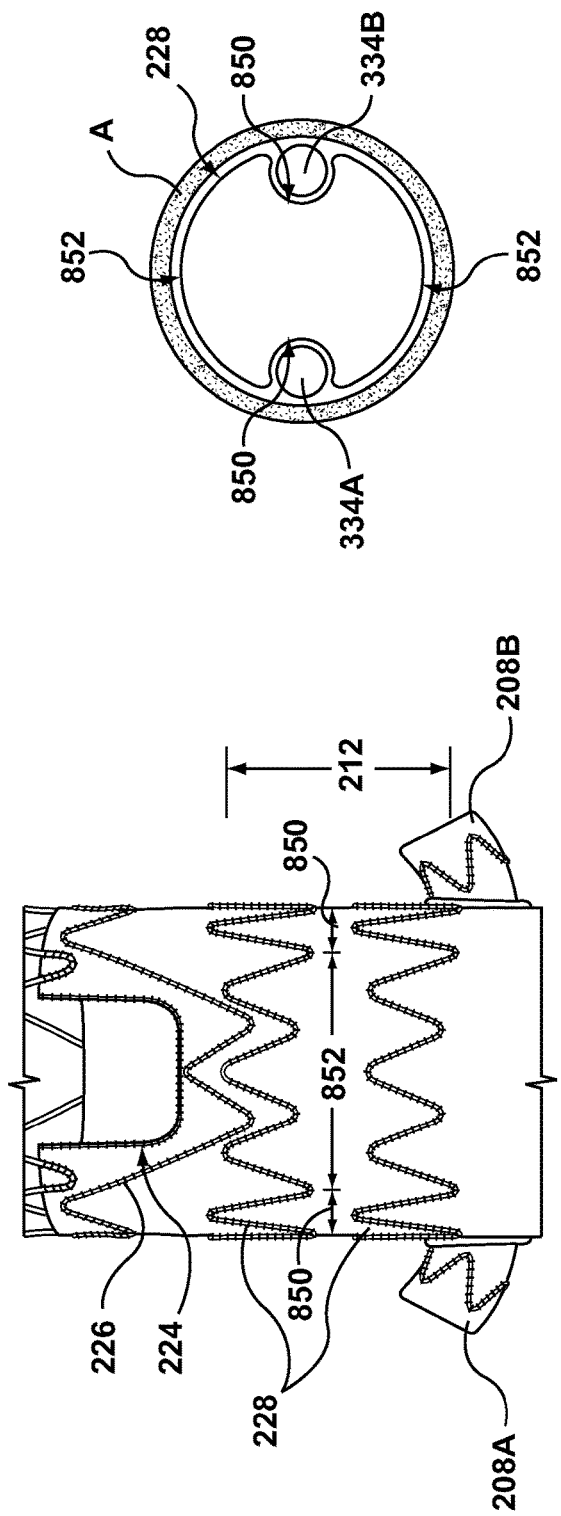
FIG. 8 illustrates an enlarged or zoomed-in view of a suprarenal body section of the main vessel stent-graft of FIG. 2.
FIG. 8A illustrates a cross-sectional view of FIG. 8, wherein the main vessel stent-graft vessel prosthesis is disposed within an aorta A and branch prostheses are disposed adjacent thereto.
FIG. 9 illustrates a variable stiffness body stent of the suprarenal body section of FIG. 8, wherein the variable stiffness body stent is laid out flat for illustrative purposes.

FIG. 8 illustrates an enlarged or zoomed-in view of suprarenal body section 212 of tubular body 202. Suprarenal body section 212 having at least one body stent 228 of variable stiffness to accommodate or conform around branch vessel prostheses that are delivered and deployed adjacent to an outside surface of main vessel stent-graft 200. In the embodiment depicted in FIG. 8, stent-graft prosthesis 200 includes a series of two independent or separate variable stiffness body stents 228. Although shown with two variable stiffness body stents, it will be understood by those of ordinary skill in the art that stent-graft prosthesis 200 may include a greater or smaller number of variable stiffness body stents 228 depending upon the desired length of suprarenal body section 212 and/or the intended application thereof. Each variable stiffness body stent 228 is a radially-compressible ring or scaffold that is coupled to tubular body 202 for supporting the graft material and is operable to self-expand into apposition with an interior wall of a body vessel (not shown). Each variable stiffness body stent 228 is constructed from a self-expanding or spring material, such as nitinol, and is a sinusoidal patterned ring including a plurality of crowns or bends 944 and a plurality of struts or straight segments 942 with each crown being formed between a pair of opposing struts as shown in FIG. 9. Variable stiffness body stents 228 may be formed from a single, continuous wire that may be solid or hollow and have a circular cross-section. In an embodiment, the wires that form variable stiffness body stents 228 have a diameter between 0.011-0.015 inches. Each variable stiffness body stent 228 is coupled to tubular body 202 distal to seal stent 226, between first end 203 thereof and opposing couplings 208A, 208B. Each variable stiffness body stent 228 is coupled to tubular body 202 by stitches or other means known to those of skill in the art. In the embodiment shown in FIG. 8, variable stiffness body stents 228 are coupled to an outside surface of tubular body 202. However, variable stiffness body stents 228 may alternatively be coupled to an inside surface of tubular body 202. Variable stiffness body stents 228 have sufficient radial spring force and flexibility to conformingly engage suprarenal body section 212 of tubular body 202 with the blood vessel inner wall.

In order to accommodate branch vessel prostheses that are delivered and deployed adjacent to an outside surface of main vessel stent-graft 200 as shown in FIG. 5, the stiffness or radial force of body stents 228 is not uniform along the circumference thereof. Rather, the radial force of body stents 228 varies along the circumference thereof. More particularly, variable stiffness body stent 228 includes two opposing regions or zones 850 having greater flexibility and less radial force as compared to the rest of the stent. As best shown in FIG. 9, which illustrates a variable stiffness body stent 228 laid flat out for illustrative purposes, variable stiffness body stent 228 includes four consecutive integral regions or zones, a first zone 850 of greater flexibility and less radial force, a second zone 852 of less flexibility and greater radial force, a third zone 850 of greater flexibility and less radial force, and a fourth zone 852 of less flexibility and greater radial force. Thus, variable stiffness body stent 228 including alternating or interchanging zones of flexibility. In an embodiment, each zone is approximately 90 degrees of the 360 degree circumference of body stent 228. "Approximately 90 degrees" as used herein includes zones ranging between 80 and 100 degrees of the circumference of the body stent. Zones 850 of greater flexibility and less radial force are approximately circumferentially aligned with and longitudinally positioned proximal of couplings 208A, 208B. "Approximately circumferentially aligned" as used herein includes zones 850 circumferentially aligned 45 degrees to −45 degrees from couplings 208A, 208B. When branch vessel prostheses are delivered and deployed through the couplings in situ, the branch vessel prostheses contact and abut against the outer surface of main vessel stent-graft 200 at zones 850. Since zones 850 have greater flexibility, zones 850 conform to the branch vessel prostheses and allow the branch vessel prostheses to longitudinally extend next to or alongside of the main vessel stent-graft without collapsing or being crushed by the radial force of the main vessel stent-graft prosthesis. Stated another way, zones 850 of body stent 228 allow for patency of the branch vessel prostheses. Body stent 228 is thus modified to alternating zones of lower radial force and greater flexibility to better accommodate branch vessel prostheses 334A, 334B while maintaining high radial force and apposition in the rest of the stent, as shown schematically in FIG. 8A in which main vessel stent-graft vessel prosthesis 200 is disposed within an aorta A and branch prostheses 334A, 334B are disposed next to or alongside of zones 850 of variable stiffness body stent 228. In addition, by tightly conforming to the branch vessel prostheses as shown in FIG. 8A, the patency of main vessel stent-graft 200 is maximized to allow maximum blood flow there through.

In order to accomplish the differing flexibility and radial force, struts 942A of zones 850 are relatively longer than struts 942B of zones 852. Elongating struts 942A as compared to struts 942B provide zones 850 with less radial force and greater flexibility. In comparison, relatively shorter struts 942B of zones 852 have less flexibility but greater radial force to ensure that zones 852 seal against the interior wall of a body vessel. In an embodiment, the length of relatively shorter struts 942B may range between 6-7 mm and the length of relatively longer struts 942A may range between 8.5-9.5 mm.

In another embodiment hereof shown in FIG. 10, a variable stiffness body stent 1028 has alternating zones of flexibility accomplished by varying the thickness of the struts. More particularly, struts 1042B of less flexible zones 1052 are thicker than struts 1042A of more flexible zones 1050. Thinner struts 1042A provide zones 1050 with less radial force and greater flexibility to accommodate branch vessel prostheses as described above while thicker struts 1042B provide zones 1052 with more radial force for sealing against the interior wall of a body vessel. In an embodiment, the thickness of relatively thicker struts 1042B may range between 0.013-0.018 inches and the thickness of relatively thinner struts 942A may range between 0.011-0.013 inches. In an embodiment, each body stent 228 may be constructed from a single continuous wire having a diameter of thinner struts 1042A, and zones 1052 having thicker struts 1042B are formed via a series of relatively short tubes slid over the continuous wire. In another embodiment, each body stent 228 is constructed from a single continuous wire having varying thicknesses to result in zones 850, 852. The lengths are struts 942A, 942B are uniform around the circumference of variable stiffness body stent 1028. Other variations or modification of portions of the stents may be used to create zones with different flexibilities.

FIG. 11 illustrates an enlarged or zoomed-in view of branch connection section 214 of tubular body 202. Branch connection section 214 includes opposing couplings 208A, 208B for connecting stent-graft prosthesis 200 to branch vessel prosthesis 334 (shown in FIGS. 3-5) to accommodate the right and left renal arteries, respectively. Referring also to the schematic view of FIG. 11A in which the stents are removed for illustrative purposes, tubular body 202 includes opposing fenestration or openings 1160 formed through a sidewall of the graft material. Openings 1160 may be circular or elliptical in shape.

Couplings 208A, 208B are disposed on an outside surface of main vessel stent-graft 200 corresponding to openings 1160 in tubular body 202. Couplings 208A, 208B are generally cylindrical in shape, and include graft material 1162 having a base 1166 and a top 1168. Graft material 1162 may be the same type of graft material as the graft material of tubular body 202 or it may be a different material. In the embodiment shown, couplings 208A, 208B are separate portions that are attached to tubular body 202. However, it would be understood by those of ordinary skill in the art that couplings 208A, 208B may be formed as a continuation of tubular body 202. Although couplings 208A, 208B are described as generally cylindrical in shape, bases 1166 are preferably elliptical rather than circular. Each base 1166 may have, for example and not by way of limitation, a long axis of approximately 8-10 mm and a short axis of approximately 5-8 mm. Further, the length of each coupling may be approximately 10-15 mm and the diameter of the top 1168 of each coupling may be approximately 5-8 mm. As shown in FIG. 11B, a wire shaped as a circle or ring 1167 may be disposed at top 1168 and at base 1166, for example by folding graft material over ring 1167 and stitching the folded over portion of the graft material to itself. In one embodiment, ring 1167 is formed from a radiopaque material in order to aid in positioning couplings 208A, 208B adjacent to or near the renal arteries. A suitable radiopaque material includes any relatively heavy metal which is generally visible by X-ray fluoroscopy such as tantalum, titanium, platinum, gold, silver, palladium, iridium, and the like.

As shown in FIGS. 2 and 11, a self-expanding support stent or sinusoidal ring 1170 may be disposed on and coupled to graft material 1162. Support stent 1170 is constructed from a self-expanding or spring material, such as nitinol, and is a sinusoidal patterned ring including a plurality of crowns or bends 1144 and a plurality of struts or straight segments 1142 with each crown being formed between a pair of opposing struts. In an embodiment, support stent 1170 is a four peak stent and thus includes eight crowns 1144 although it will be apparent to one of ordinary skill in the art that the support stent may include more or fewer crowns. Support stents 1170 are coupled to graft material 1162 distal to or under tops 1168 of couplings 208A, 208B by stitches or other means known to those of skill in the art. In the embodiment shown in FIG. 11, support stents 1170 are coupled to an outside surface of graft material 1162. However, support stents 1170 may alternatively be coupled to an inside surface of graft material 1162. Support stents 1170 may be formed from a single, continuous wire that may be solid or hollow and have a circular cross-section. In an embodiment, the wires that form support stents 1170 have a diameter between 0.006-0.008 inches. In another embodiment, the cross-section of the wires that form support stents 1170 may be an oval, square, rectangular, or any other suitable shape. Support stents 1170 ensure that lumens 1164 defined by couplings 208A, 208B are open such that the branch vessel prostheses may be delivered there through, thereby facilitating cannulation of the branch vessels. Support stents 1170 also serve to elevate and/or orient tops 1168 of couplings 208A, 208B towards the ostia of the right and left renal arteries during and after deployment to ensure that the unsupported material would not collapse and lead to seal performance concerns. Due to the energy stored in the shape memory material of support stent 1170 while in the delivery system, couplings 208A, 208B pop out or away from tubular body 202 of main vessel stent-graft 200 when released from a sleeve (delivery system) during delivery and deployment. This prevents bunching, kinking, collapse or eversion of the couplings 208A, 208B when released from the delivery system.

As shown in FIG. 5, couplings 208A, 208B are configured for placement in situ distal to the renal arteries. Tops 1168 of couplings 208A, 208B are configured for placement adjacent to or below the ostia of the renal arteries but tops 1168 do not extend into the ostia. Couplings 208A, 208B are sufficiently flexible in directions transverse to their longitudinal axis. This mobility is due to the shape of couplings 208A, 208B and can be further improved by utilizing some excess graft material 1162 when forming couplings 208A, 208B. It is not required that main vessel stent-graft prosthesis 200 be circumferentially aligned with the renal arteries, because the top 1168 of each coupling is allowed to land distal and circumferentially offset to its respective renal artery ostium with the branch stent-graft prosthesis, in combination with variable stiffness body stents 228, providing connections between couplings 208A, 208B and its respective renal artery. Accordingly, couplings 208A, 208B are only required to be roughly or approximately circumferentially aligned with the ostia of the renal arteries. "Approximately circumferentially aligned" as used herein includes couplings 208A, 208B circumferentially aligned 45 degrees to −45 degrees from right and left renal arteries, respectively. By eliminating the need to precisely position couplings 208A, 208B with respect to the ostia of the renal arteries, main vessel stent-graft 200 may be used on a multitude of patients having a range of anatomies. This also allows for main vessel stent-graft 200 to treat a variety of patients in a truly "off-the shelf" manner, eliminating the 6-8 week lead time associated with custom fenestrated devices. In addition, the process of delivering and positioning main vessel stent-graft 200 is improved.

When branch vessel prostheses 334A, 334B are delivered and deployed through lumens 1164 of couplings 208A, 208B into the right and left renal arteries, respectively, the couplings are sandwiched between an outer surface of main vessel stent-graft 200 and an interior wall of the abdominal aorta. Branch vessel prostheses 334A, 334B extend out of the tops of the couplings and into the right and left renal arteries, respectively. The more flexible zones 850 of variable stiffness body stents 228 conform or give way to couplings 208A, 208B having expanded branch vessel prostheses 334A, 334B therein, thereby resulting in tubular body 202 having a narrower midsection or waist when deployed in situ, as shown in FIG. 8A. The outer diameter of tubular body 202 is reduced or contracted next to couplings 208A, 208B having expanded branch vessel prostheses 334A, 334B therein.

Figure 12A:
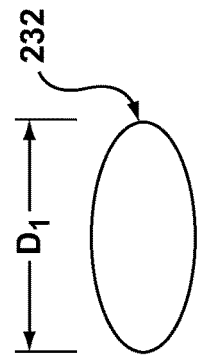
FIG. 12 illustrates an enlarged or zoomed-in view of a distal half or bottom of the main vessel stent-graft of FIG. 2, with FIG. 12A being a cross-sectional view taken along line A-A of FIG. 12 (showing only the stent cross-section for clarity) and FIG. 12B being a cross-sectional view taken along line B-B of FIG. 12 (showing only the stent cross-section for clarity).
Figure 12B:
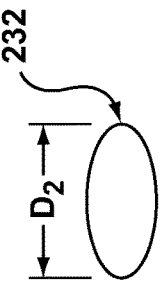
Figure 12:
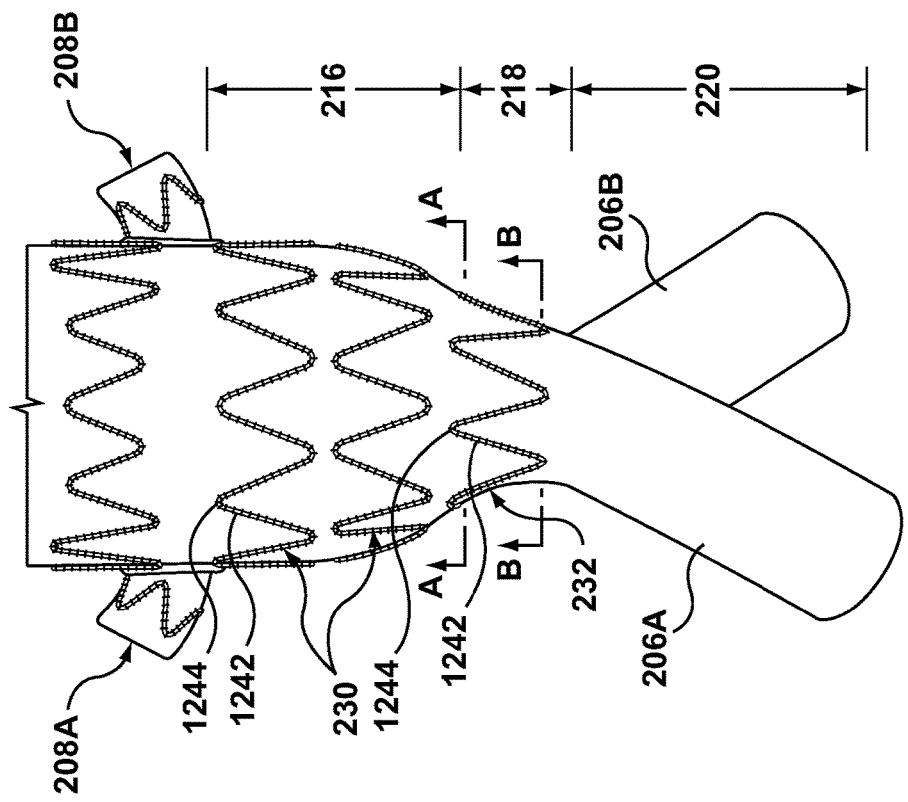

FIG. 12 illustrates an enlarged or zoomed-in view of infrarenal body section 216 and transition or distal end section 218 of tubular body 202, as well as bifurcated portion 220. Infrarenal body section 216 includes at least one body stent 230. In an embodiment, the stiffness or radial force of body stents 230 is uniform along the circumference thereof, although such uniform stiffness/radial force is not required. In the embodiment depicted in FIG. 12, stent-graft prosthesis 200 includes two independent or separate body stents 230. Although shown with two body stents 230, it will be understood by those of ordinary skill in the art that stent-graft prosthesis 200 may include a greater or smaller number of body stents 230 depending upon the desired length of infrarenal body section 216 and/or the intended application thereof. Each body stent 230 is a radially-compressible ring or scaffold that is coupled to tubular body 202 for supporting the graft material and is operable to self-expand. Each body stent 230 is constructed from a self-expanding or spring material, such as nitinol, and is a sinusoidal patterned ring including a plurality of crowns or bends 1244 and a plurality of struts or straight segments 1242 with each crown being formed between a pair of opposing struts as shown in FIG. 12. Body stents 230 may be formed from a single, continuous wire that may be solid or hollow and have a circular cross-section. In an embodiment, the wires that form body stents 230 have a diameter between 0.010-0.013 inches. In another embodiment, the cross-section of the wires that form body stents 230 may be an oval, square, rectangular, or any other suitable shape. Each body stent 230 is coupled to tubular body 202 distal of couplings 208A, 208B. Each body stent 230 is coupled to tubular body 202 by stitches or other means known to those of skill in the art. In the embodiment shown in FIG. 12, body stents 230 are coupled to an outside surface of tubular body 202. However, body stents 230 may alternatively be coupled to an inside surface of tubular body 202.

Transition or distal end section 218 also includes at least one body stent 232. Body stent 232 is similar to body stents 230, except that body stent 232 is tailored to transition tubular body 202 into bifurcated portion 220. As stated herein, with reference to FIG. 2, bifurcated portion 220 extends from second end 205 of tubular body 202. In the embodiment shown in FIG. 12, second end 205 of tubular body 202 has a relatively larger diameter or width than a proximal end of bifurcated portion 220, and accordingly body stent 232 has a variable expanded outer diameter or width that decreases from a first expanded diameter D1 at a top or proximal end of body stent 232 (shown in FIG. 12A) to a second expanded diameter D2 at a bottom or distal end of body stent 232 (shown in FIG. 12B). As shown in FIGS. 12A-12B, body stent 232 preferably has a generally elliptical or oval cross-section rather than circular, although body stent 232 may be circular. In another embodiment hereof (not shown), second end 205 of tubular body 202 may have relatively smaller diameter or width than a proximal end of bifurcated portion 220, and accordingly body stent 232 has a variable expanded outer diameter that increases from a top or proximal end of body stent 232 to a bottom or distal end of body stent 232. In yet another embodiment (not shown), second end 205 of tubular body 202 may have a diameter approximately equal to a proximal end of bifurcated portion 220, and accordingly body stent 232 has a constant outer diameter from a top or proximal end of body stent 232 to a bottom or distal end of body stent 232. Thus, depending on the diameter of main vessel stent-graft 200 relative to the diameter of bifurcated portion 220, the outer diameter of transition stent 232 may increase, decrease, or stay constant.

FIGS. 13-26 schematically show a method of delivering main vessel stent-graft 200 to a target site in the abdominal aorta A and a method of delivering branch vessel stent-grafts to the renal arteries. In FIGS. 13-26, a portion of abdominal aorta A is shown having a short-neck infrarenal abdominal aortic aneurysm AAA that extends below the renal arteries. In other methods in accordance with embodiments hereof, main vessel stent-graft 200 may be used treat a juxtarenal abdominal aortic aneurysm, which approaches or extends up to, but does not involve, the renal arteries, and a suprarenal abdominal aortic aneurysm, which involves and extends above the renal arteries. A right renal artery RRA and a left renal artery LRA extend from aorta A, as does the superior mesenteric artery (SMA). The described method of deployment is a staged or incremental release of main vessel stent-graft, in which delivery of the branch vessel stent-grafts to the renal arteries occurs prior to full deployment of main vessel stent-graft 200.

Figure 13:
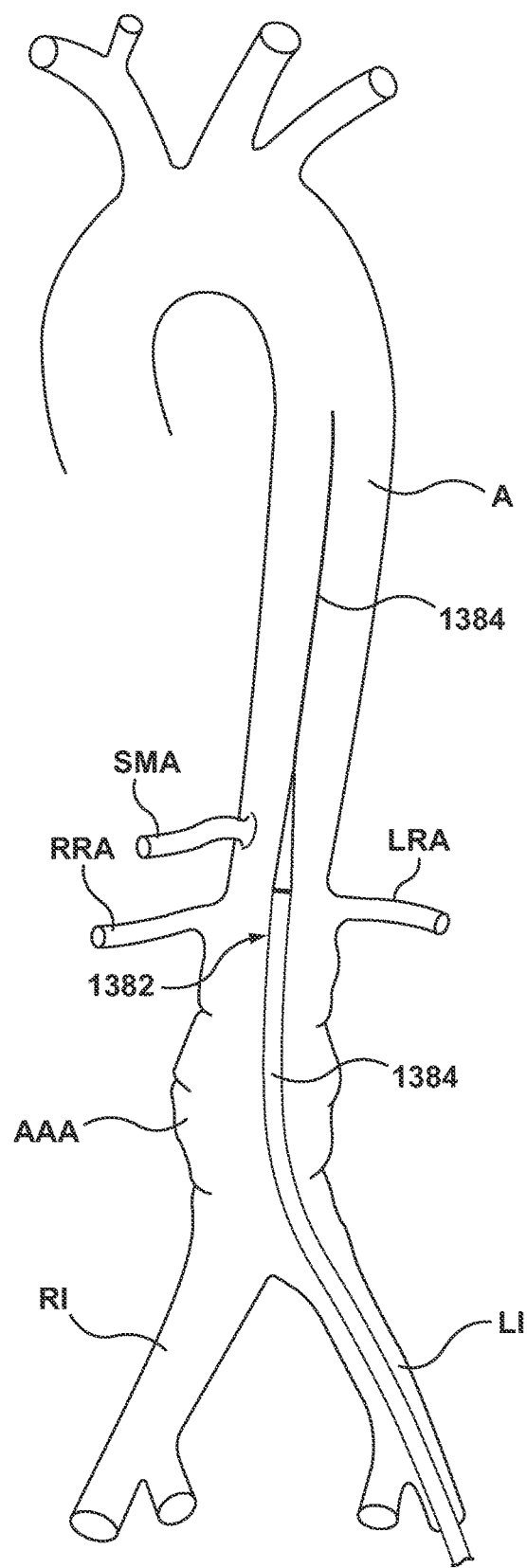
FIGS. 13-25 schematically show a method of delivering the main vessel stent-graft of FIG. 2 to a target site in the abdominal aorta and a method of delivering branch vessel stent-grafts of FIG. 3 to the renal arteries.

FIG. 13 shows a main vessel delivery system 1382, with main vessel stent-graft 200 compressed therein, advanced over a main vessel guide wire 1384 and to the target site in the abdominal aorta A. Guide wire 1384 is typically inserted into the femoral artery and routed up through the left iliac artery LI to abdominal aorta, as is known in the art. The function and structure of delivery system 1382 are discussed in detail in U.S. patent application Ser. No. 13/457,541 to Argentine et al., Ser. No. 13/457,535 to Maggard et al., Ser. No. 13/457,537 to Argentine et al., and Ser. No. 13/457,544 to Maggard et al., which were filed on a date concurrent herewith and is incorporated by reference herein in its entirety, and therefore only certain features thereof will be described herein to illustrate the deployment of main vessel stent-graft 200. The location of the main delivery system 1382 and/or the main vessel stent-graft 200 may be verified radiographically and delivery system 1382 and/or stent-graft 200 may include radiopaque markers as known in the art. For example, in an embodiment, proximal end section 210 and/or couplings 208A, 208B of main vessel stent-graft 200 may include radiopaque markers to aid in positioning. Main vessel stent-graft 200 is mounted on a catheter shaft 1488 (see FIG. 14) of the delivery system and an outer delivery sheath 1386 of the delivery system covers and restrains main vessel stent-graft 200 in a compressed configuration for delivery thereof. As will be understood by those of ordinary skill in the art, delivery system 1382 may include a tip capture mechanism (not shown) which engages the proximal-most set of crowns of anchor stent 222 until retraction of the tip capture mechanism releases the proximal-most set of crowns for final deployment of main vessel stent-graft 200.

Figure 14:
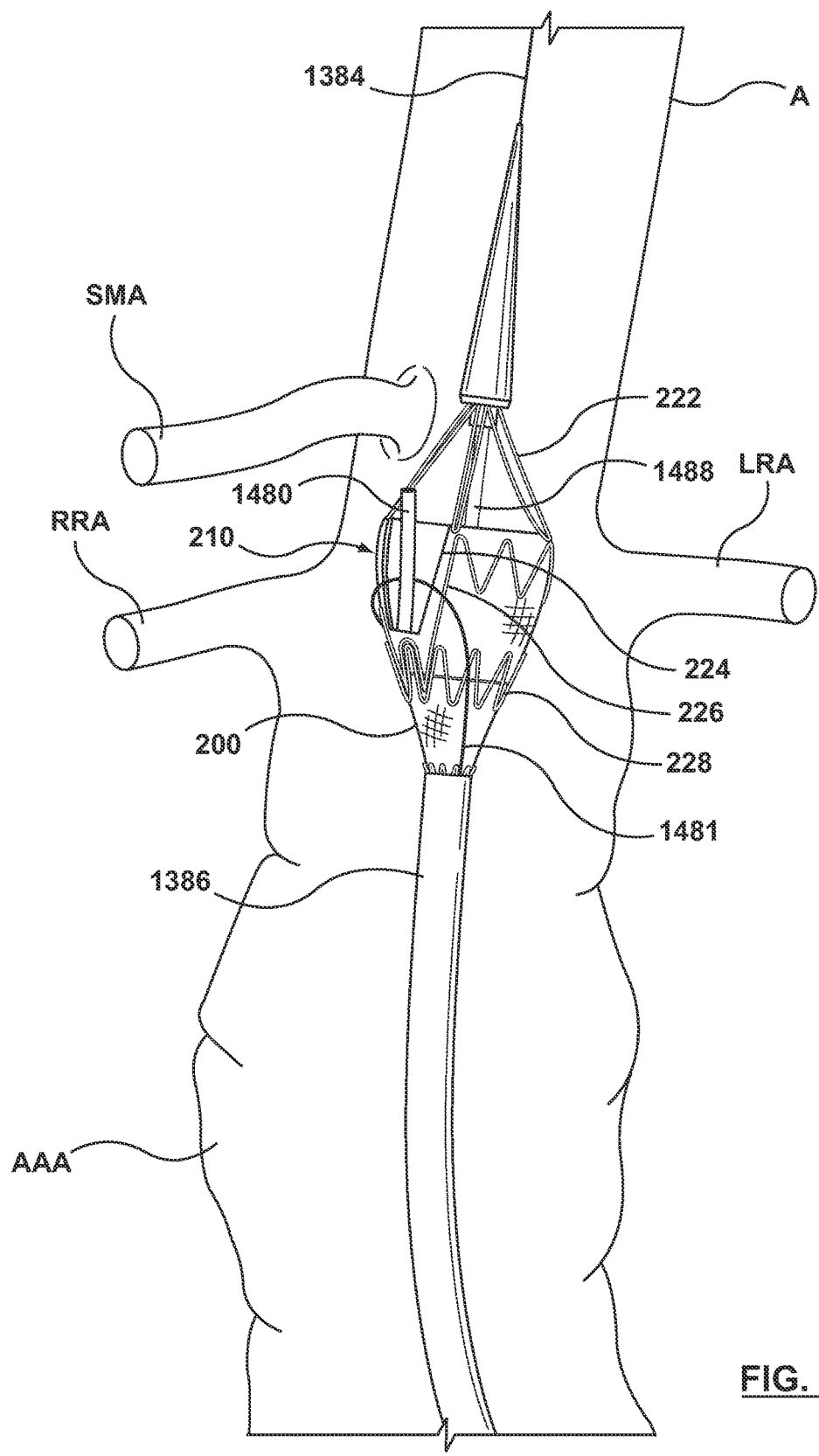

FIG. 14 illustrates a first or initial step to deploy main vessel stent-graft 200 in which outer delivery sheath 1386 of delivery system 1382 is retracted to release or uncover proximal end section 210 of main vessel stent-graft 200. As shown in FIG. 14, when first released from the delivery system, proximal end section 210 may be positioned such that scallop 224 is distal to the target site of the superior mesenteric artery (SMA). Alternatively, proximal end section 210 may be positioned such that scallop 224 is aligned directly with the SMA. The proximal-most set of crowns of anchor stent 222 is captured or restrained by the tip capture mechanism of delivery system 1382. Delivery sheath 1386 is retracted to expose at least seal stent 226 and can be retracted past couplings 208A, 208B but still constrains at least bifurcated portion 220 including legs 206A, 206B. In the embodiment of FIG. 14, delivery sheath 1386 is shown as retracted to expose a first variable stiffness body stent 228. A retractable tube 1480 and an anchoring wire 1481 extending through and/or over scallop 224 are portions of delivery system 1382, and are utilized in positioning main vessel stent-graft 200 with respect to the SMA by aiding in cannulation as described in co-pending U.S. patent application Ser. No. 13/457,541 to Argentine et al., Ser. No. 13/457,535 to Maggard et al., Ser. No. 13/457,537 to Argentine et al., and Ser. No. 13/457,544 to Maggard et al., previously incorporated by reference in their entirety. Retractable tube 1480 is preloaded through the delivery system and main vessel stent-graft 200 prior to introduction into the vasculature. More particularly, retractable tube 1480 has an inner diameter sized to receive a guidewire. Retractable tube 1480 extends though the delivery system, through main vessel stent-graft 200, and exits main vessel stent-graft 200 through scallop 224. By preloading retractable tube 1480 rather than a guidewire itself, a physician may select the particular dimensions or properties of the guidewire and catheter combination to be used in a procedure.

Figure 15:
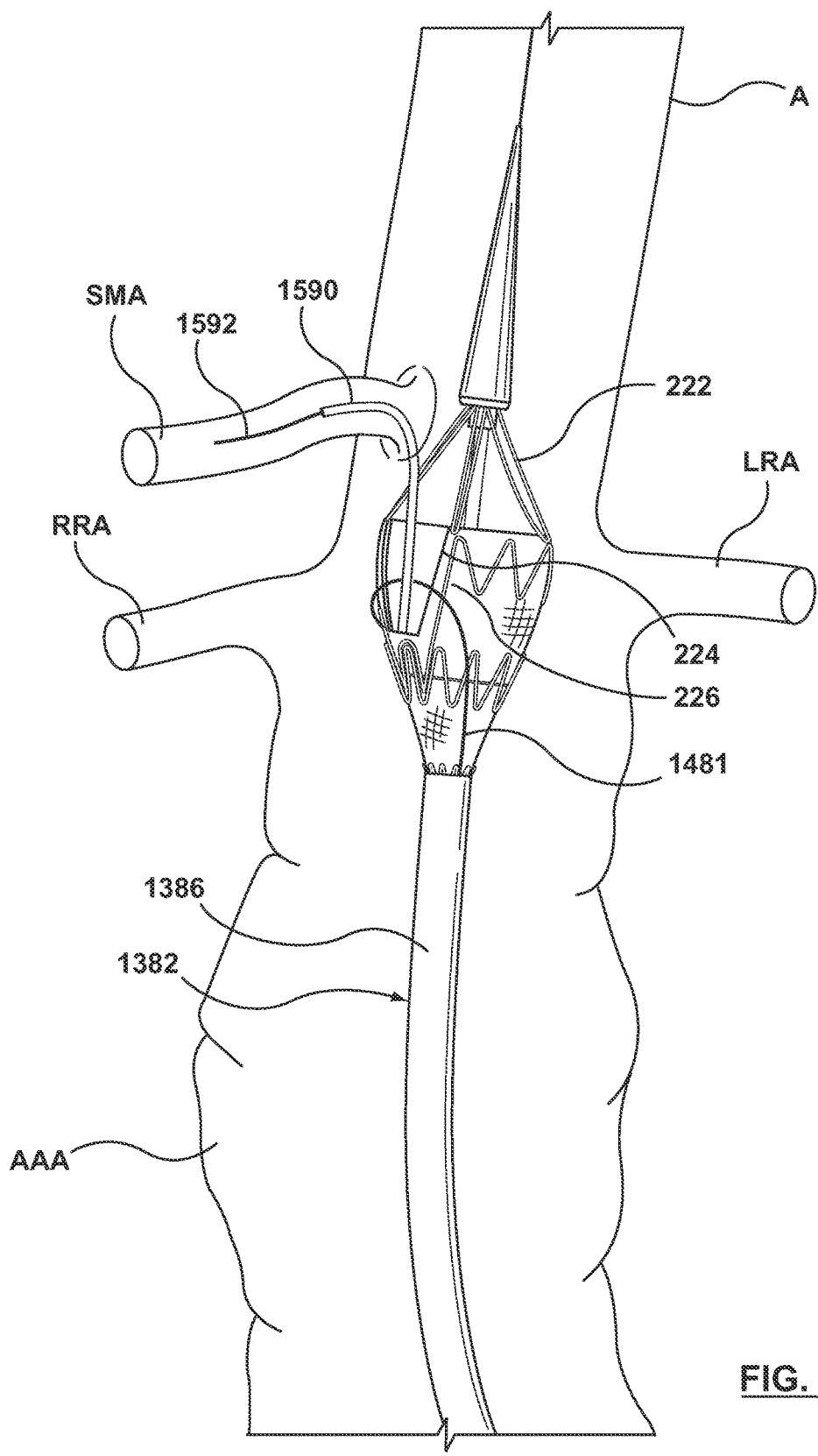

FIG. 15 depicts the cannulation of the SMA to scallop 224 of main vessel stent-graft with an ostium of the SMA, wherein "cannulation" and "cannulate" are terms that are used herein with reference to the navigation of a guidewire and guide catheter into a target vessel. More particularly, in order to cannulate the SMA, a guidewire 1592 is inserted through retractable tube 1480 of delivery system 1382 and advanced until in the thoracic aorta. The retractable tube 1480 is then removed from the delivery system. A curved guide catheter 1590 is then delivered over indwelling guide wire 1593 to be proximal to the SMA ostium. The guidewire 1593 and curved guide catheter 1590 are then used in conjunction via manipulation by the operator to cannulate the vessel, as shown in FIG. 15. Guide wire 1592 and catheter 1590 may remain positioned through the SMA during the remaining deployment steps in order to maintain positioning and alignment of main vessel stent-graft prosthesis 200, particularly scallop 224.

Figure 16:
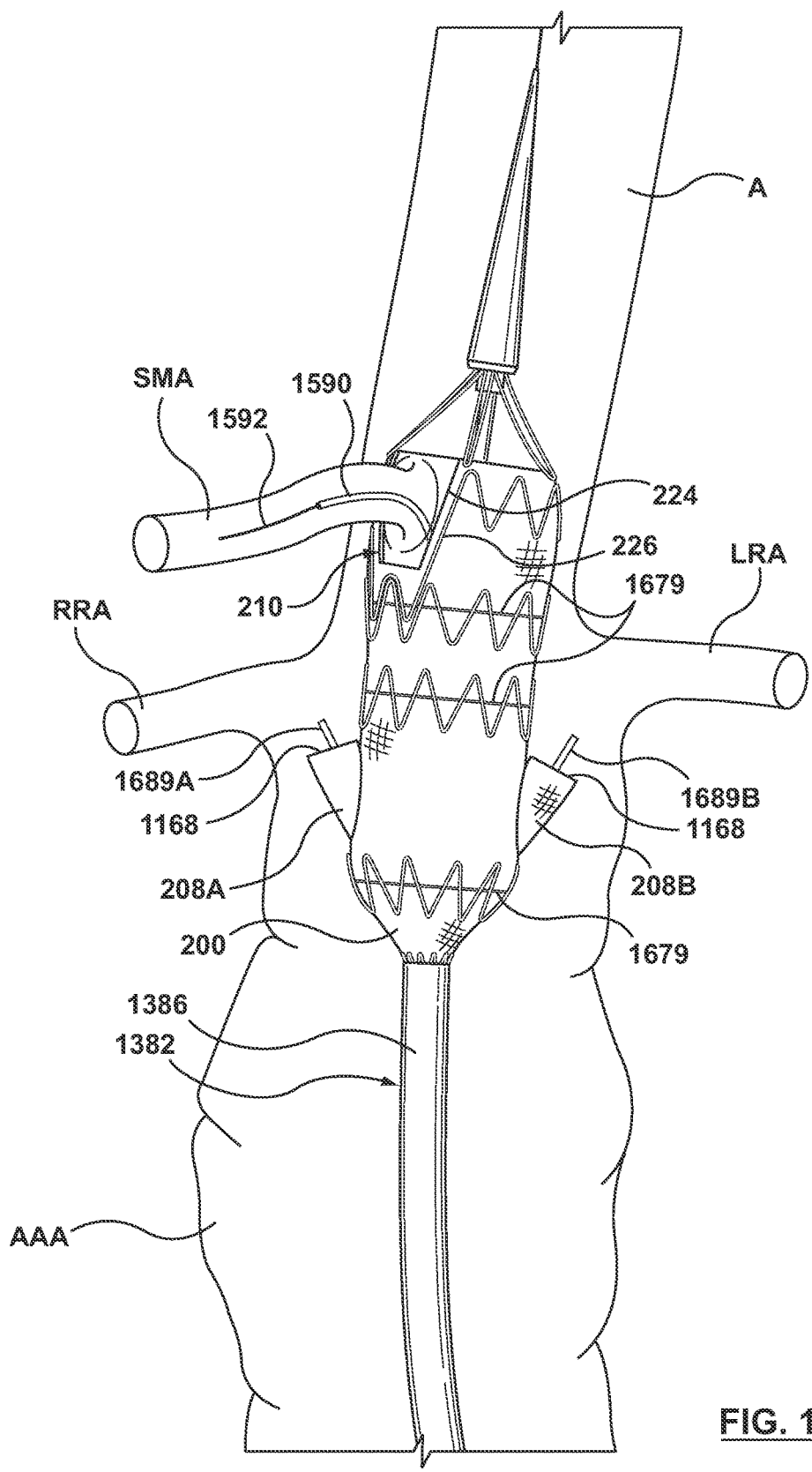
Figure 17:
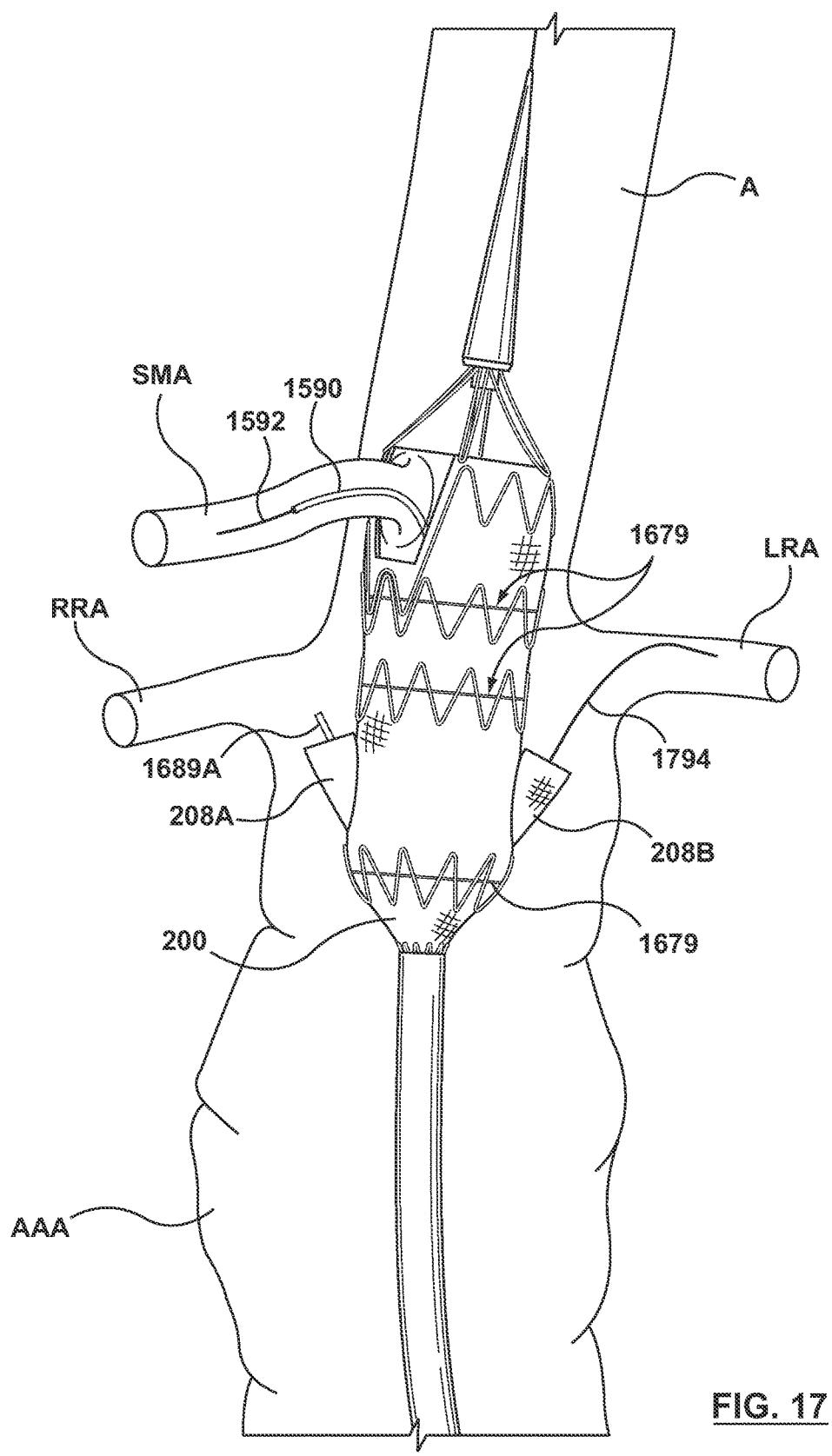

Delivery system 1382 is then advanced until scallop 224 frames or aligns with the ostium of the SMA, as shown in FIG. 16. As previously stated, proximal end section 210 of main vessel stent-graft 200 may include radiopaque markers to aid in positioning of scallop 224 such that scallop 224 extends around the ostium of the superior mesenteric artery (SMA). For example, as described above with reference to FIG. 6A, scallop 224 may include a U-shaped wire formed from a radiopaque material in order to aid in positioning scallop 224 around the SMA.

In addition to aligning scallop 224 with the SMA, FIG. 16 also depicts main vessel stent-graft 200 having been released from delivery sheath 1386 to below couplings 208A, 208B of main vessel stent-graft 200 if this had been elected to not be deployed earlier, as described above. Release of couplings 208A, 208B from delivery sheath 1386 also exposes retractable tubes 1689A, 1689B that are preloaded through the delivery system and main vessel stent-graft 200 prior to introduction into the vasculature, similar to retractable tube 1480 described above. Retractable tubes 1689A, 1689B extend though the delivery system, through main vessel stent-graft 200, and exit out of couplings 208A, 208B, respectively, of main vessel stent-graft 200. The exposed ends of elongate retractable tubes 1689A, 1689B are generally or approximately aligned with renal arteries RRA, LRA, respectively. Anchor stent 222 is still captured or restrained by the tip capture mechanism of delivery system 1382. When released from outer sheath 1386, couplings 208A, 208B are positioned distal to the renal arteries. Tops 1168 of couplings 208A, 208B are positioned adjacent to or distal of the ostia of the renal arteries but do not extend into the ostia. As will be seen, branch vessel stent-grafts will bridge the gap or distance between couplings 208A, 208B and the renal arteries RRA, LRA. The length of the branch vessel stent-grafts may be selected by the physician, providing the ability to treat various patient anatomies.

In an embodiment, portions of main vessel stent-graft 200 are radially constrained by a plurality of circumferentially constraining sutures 1679 after retraction of delivery sheath 1386. The function and structure of circumferentially constraining sutures 1679 are discussed in detail in U.S. patent application Ser. No. 13/458,076 to Pearson et al., which was filed on a date concurrent herewith and is incorporated by reference herein in its entirety, and therefore only certain features will be described herein to illustrate the deployment of main vessel stent-graft 200. Circumferentially constraining sutures 1679 circumferentially constrain or cinch tubular body 202 of main vessel stent-graft 200 such that the main vessel stent-graft 200 is held to a constrained state that is approximately 40% to 70% smaller than the target vessel lumen. In FIGS. 14-21, main vessel stent-graft 200 is shown constrained to a lesser degree via circumferentially constraining sutures 1679, i.e., the partially constrained state of main vessel stent-graft 200 is shown with a larger diameter than would result from the stated 40% to 70% smaller than the target vessel lumen, for sake of clarity and illustrative purposes only. The use of circumferentially constraining sutures 1679 ensures that main vessel stent-graft 200 is able to be repositioned during the procedure to aid in cannulation steps. In addition, the use of circumferentially constraining sutures 1679 creates additional space between the outside surface of the radially-constrained main vessel stent-graft 200 and the vessel to allow for delivery and deployment of branch vessel prostheses to the renal arteries, as will be explained in more detail herein.

Figure 18:
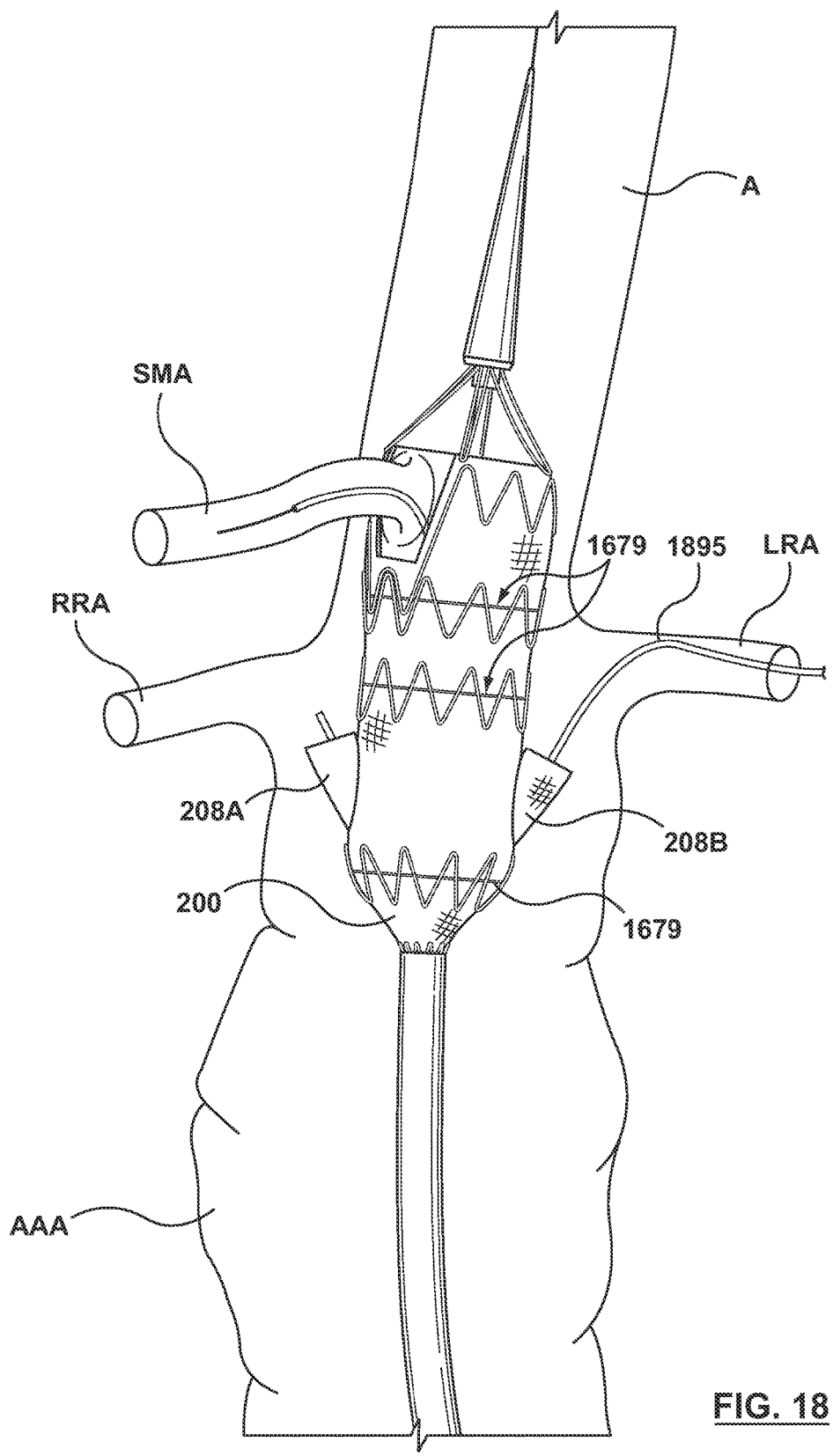
Figure 19:
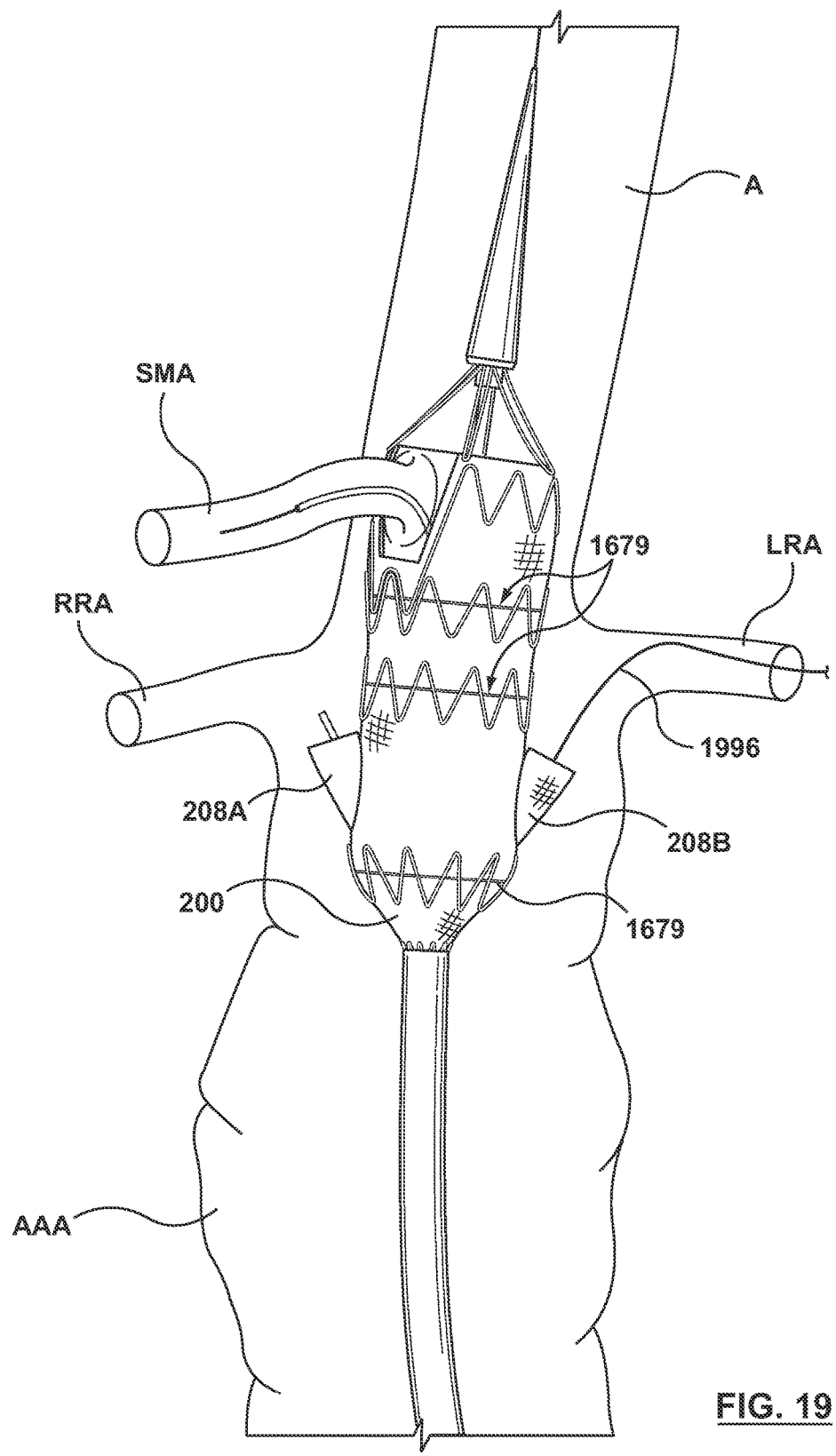
Figure 20:
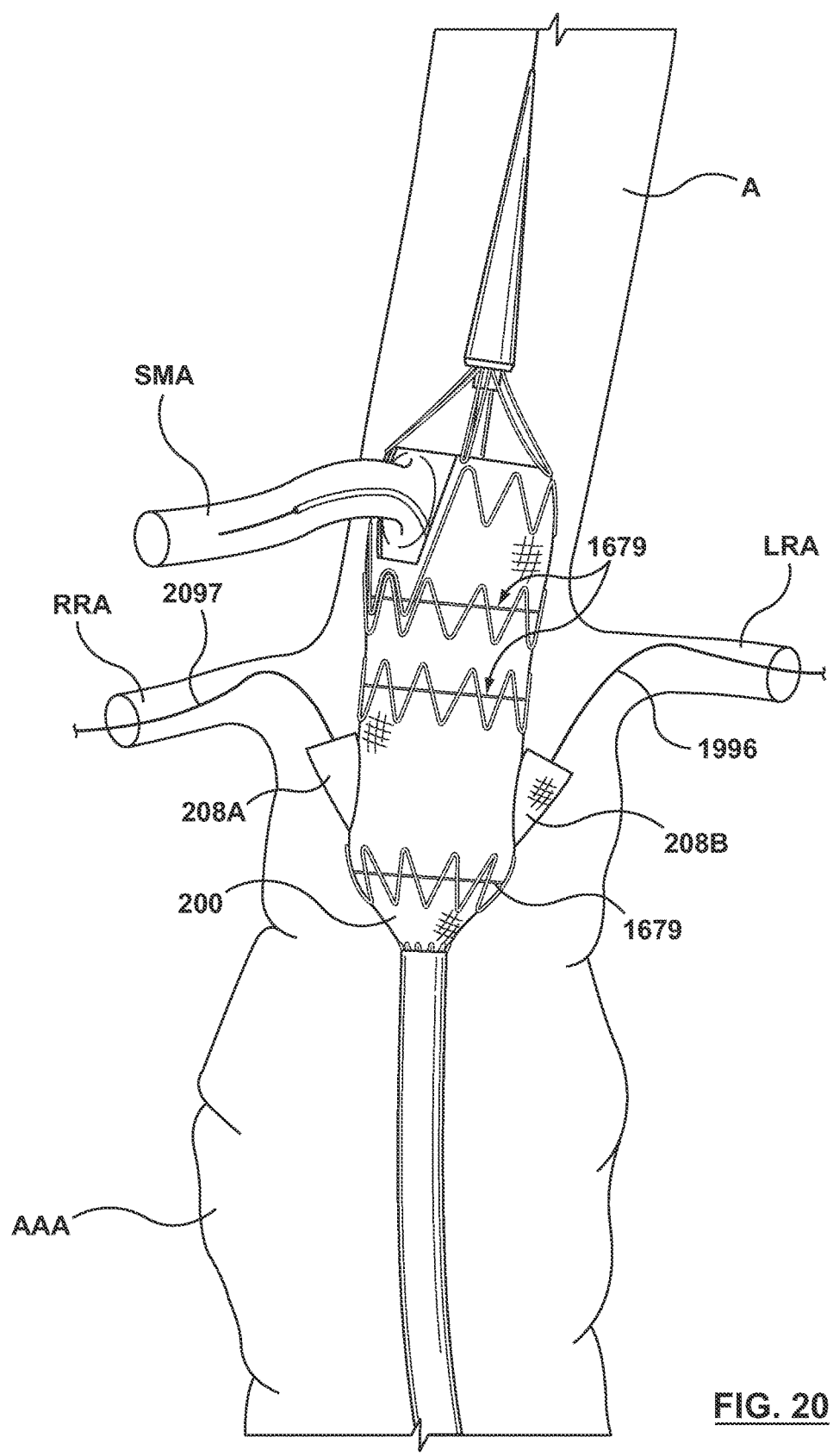

FIGS. 17-20 depict the cannulation of the right renal artery RRA and the left renal artery LRA. Initially, a guide wire 1794 is delivered through retractable tube 1689B of delivery system 1382 and tracked into the ostium of the left renal artery LRA and retractable tube 1689B is then removed from delivery system 1382 as shown in FIG. 18. Thereafter as shown in FIG. 18, a tubular sheath or guide catheter 1895 having a pre-formed curved end is advanced over wire 1794 to extend within the left renal artery LRA. The guidewire 1794 and curved guide catheter 1895 are then used in conjunction via manipulation by the operator to cannulate the vessel, and wire 1794 is then removed as shown in FIG. 19. A guidewire 1996 is tracked through a lumen of sheath 1895 until it extends within the left renal artery LRA, at which point sheath 1895 is removed from delivery system 1382 as represented in FIG. 19. The steps described for cannulating the left renal artery LRA are then repeated to cannulating the right renal artery RRA, which is shown in FIG. 20 after the final step of withdrawing a tubular sheath or guide catheter has been performed such that a guidewire 2097 is left indwelling within the right renal artery RRA. In another embodiment, the right renal artery RRA may be cannulated prior to the left renal artery LRA or the cannulation steps may be performed for both the right renal artery RRA and the left renal artery LRA concurrently.

Figure 21:
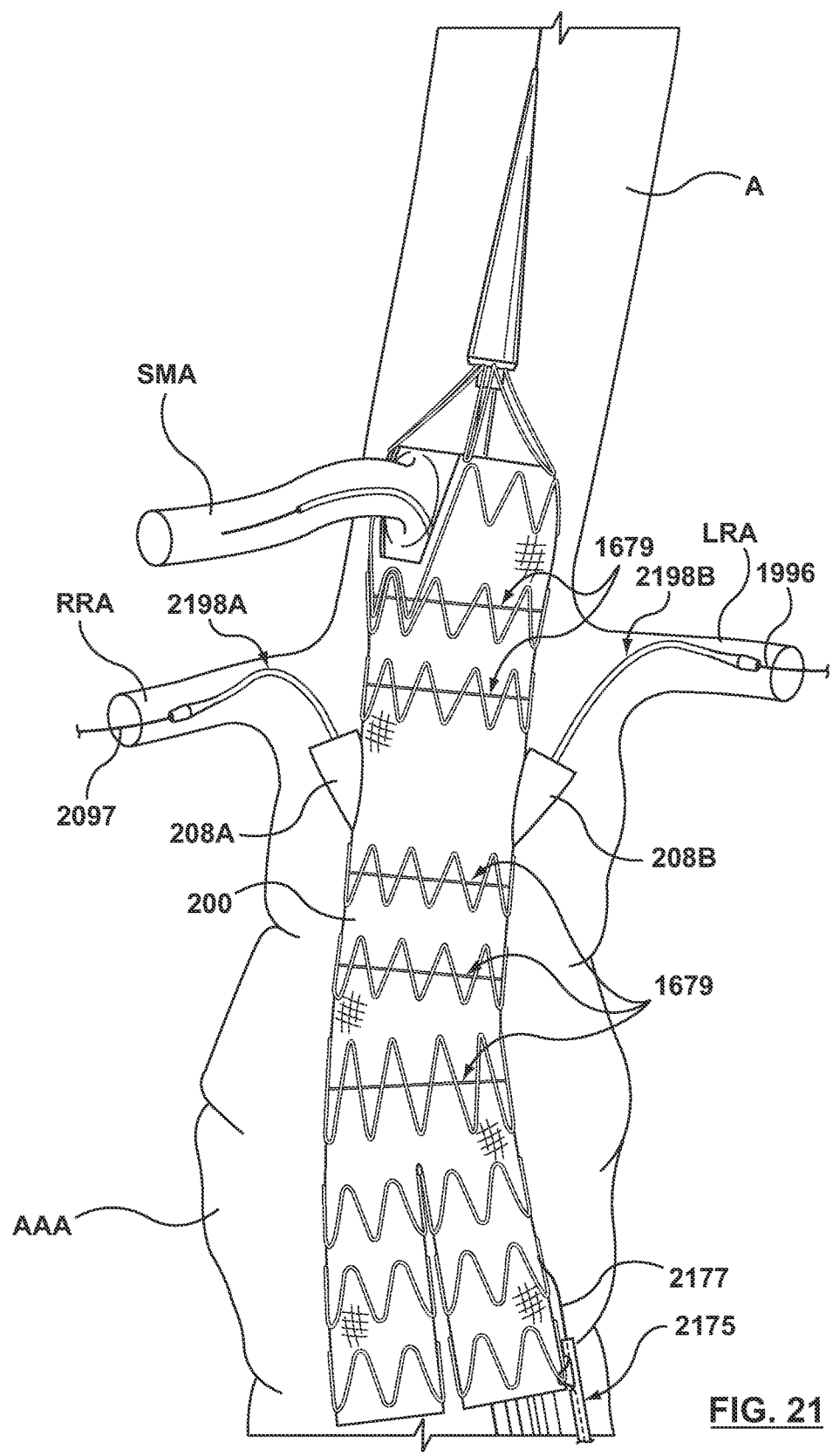

At this point, delivery sheath 1386 should be retracted to expose the full length of main vessel stent-graft 200, as also shown in FIG. 21. Main vessel stent-graft 200 remains only partially expanded or deployed due to circumferentially constraining sutures 1679 and proximal-most set of crowns of anchor stent 222 is captured or restrained by the tip capture mechanism of delivery system 1382. As shown in FIG. 21, delivery system 1382 includes a capture mechanism 2175 having one or more trigger wires 2177 for releasing the circumferentially constraining sutures 1679. In addition, although not shown in FIG. 22, a middle member portion of delivery system 1382 has been removed in order to reconfigure delivery system 1382 into a delivery sheath configuration. Distal capture mechanism 2175, trigger wires 2177, and the middle member portion of delivery system 1382 are described in more detail in U.S. patent application Ser. No. 13/457,541 to Argentine et al., Ser. No. 13/457,535 to Maggard et al., Ser. No. 13/457,537 to Argentine et al., and Ser. No. 13/457,544 to Maggard et al., previously incorporated by reference in its entirety.

After removal of the middle member portion of delivery system 1382, branch delivery catheters 2198A, 2198B are then advanced over guide wires 2097, 1996, respectively, as shown in FIG. 21. For use in embodiments hereof, branch delivery catheters 2198A, 2198B may be a stent-graft delivery system similar to that used to deliver the Complete SE stent from Medtronic, Inc. or any other comparable delivery system. Branch delivery catheters 2198A, 2198B are advanced through couplings 208A, 208B, respectively, and into right renal artery RRA and left renal artery LRA.

Figure 22:
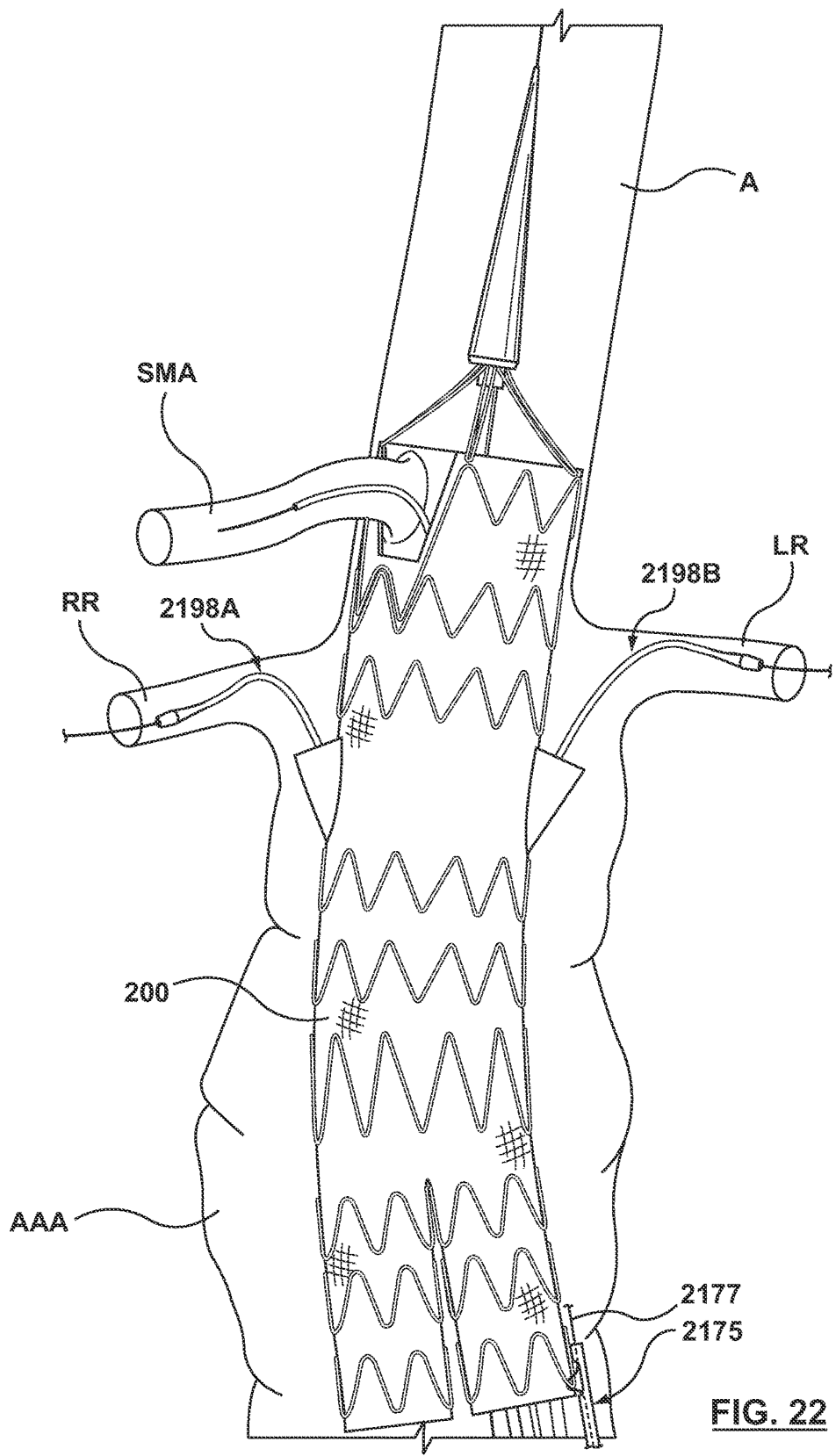
Figure 23:
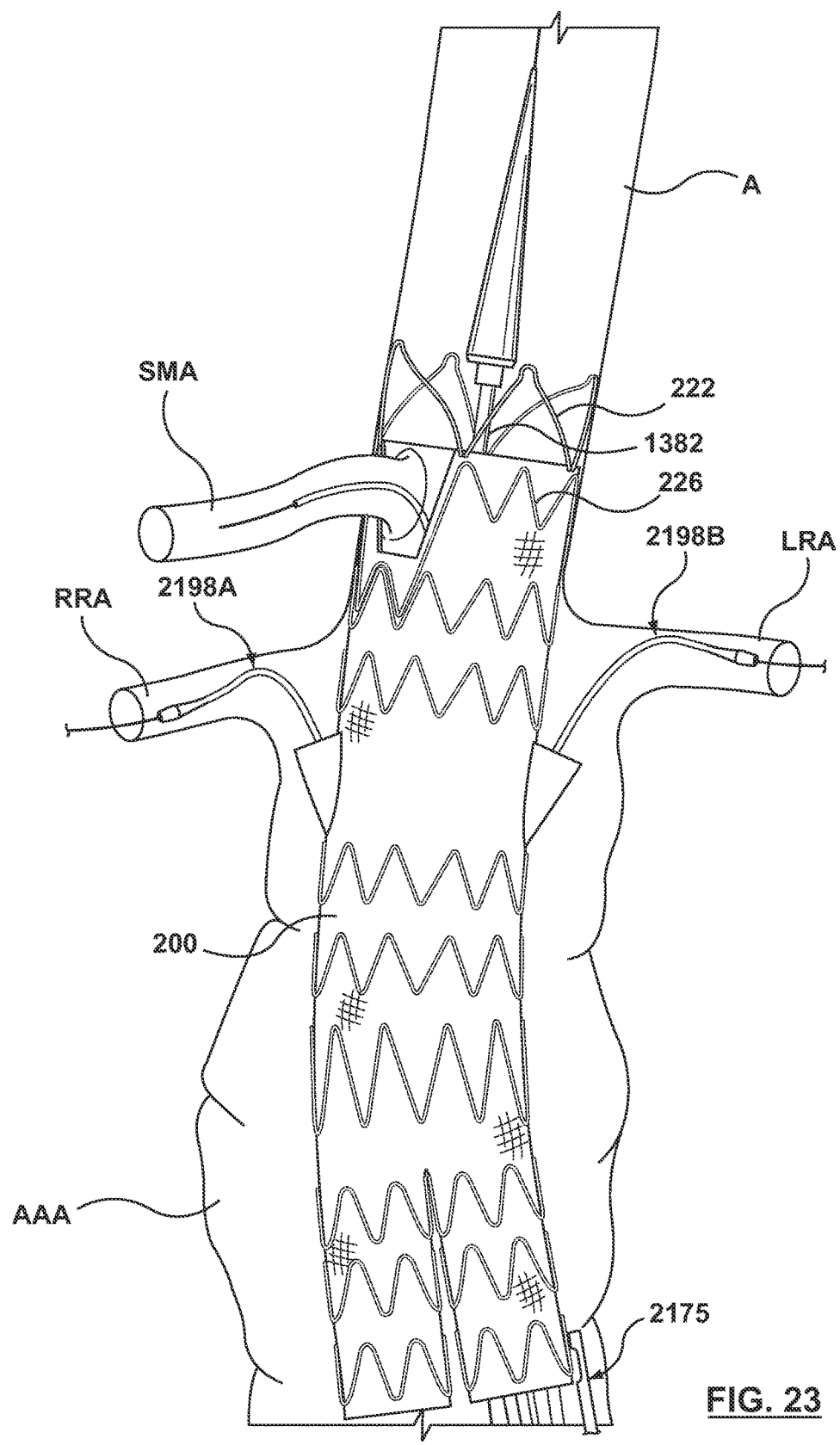

If utilized, the circumferentially constraining sutures 1679 as fully described in co-pending U.S. patent application Ser. No. 13/458,076 to Pearson et al., previously incorporated by reference in its entirety, are now released via trigger wire 2177 of capture mechanism 2175 to allow the self-expanding stents of main vessel stent-graft 200, other than anchor stent 222, to return to their fully expanded configuration as shown in FIG. 22. Anchor stent 222 may then be released from the tip capture mechanism of the delivery system 1382 into apposition with the aorta, whereby main vessel stent-graft 200 is in a fully deployed or expanded configuration free of delivery system 1382 as shown in FIG. 23. When anchor stent 222 is released from delivery system 1382, seal stent 226 fully expands and conformingly engages and seals the edges of scallop 224 with the inner wall of the aorta as described herein.

Figure 24:
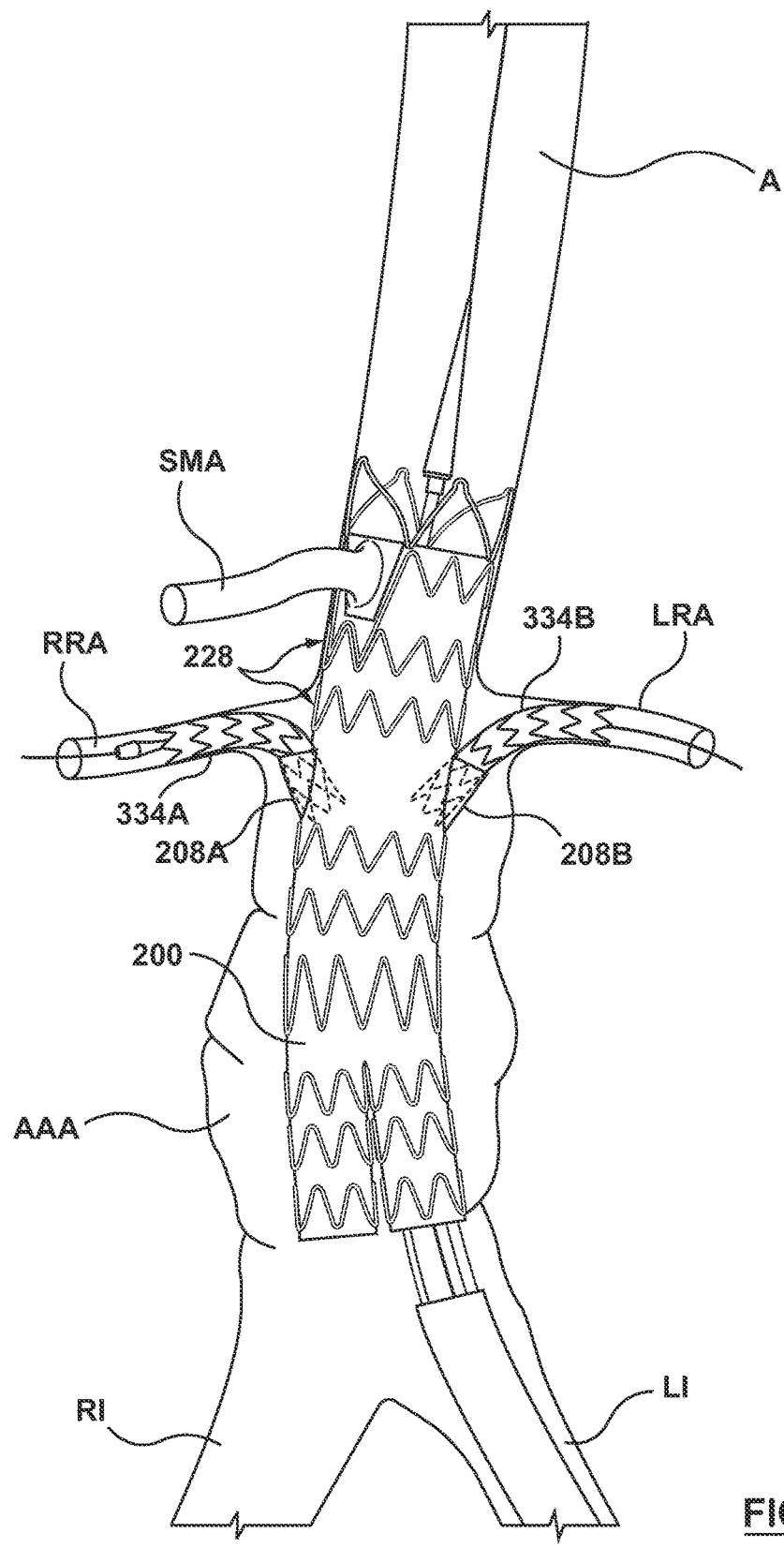

Branch vessel stent-grafts 334A, 334B may then be deployed within right renal artery RRA and left renal artery LRA, respectively. FIG. 24 depicts branch vessel stent-grafts 334A, 334B released from their respective delivery systems so that each is deployed to extend from its respective renal artery into and through its respective couplings 208A, 208B of main vessel stent-graft 200 to be anchored therein and to provide respective fluid passageways there between. For use in embodiments hereof, branch vessel stent-grafts 334A, 334B are tubes of graft material having self-expanding stent support structures and may be a tubular stent-graft such as tubular stent-grafts suitable as branches for use in the ENDURANT® stent graft system available from Medtronic, Inc. When branch vessel stent-grafts 334A, 334B are deployed, they contact and abut against the outer surface of main vessel stent-graft 200. As described herein, main vessel stent-graft 200 includes variable stiffness body stents 228/1028 that include zones of greater flexibility, positioned next to or alongside of expanded branch vessel prostheses 334A, 334B, which allows a portion of main vessel stent-graft 200 to conform to the expanded branch vessel prostheses. Thus, expanded branch vessel stent-grafts 334A, 334B longitudinally extend adjacent to main vessel stent-graft 200 without collapsing or being crushed by the relatively larger prosthesis. Variable stiffness body stents 228/1028 also include zones of less flexibility, and greater radial force, which are not aligned with expanded branch vessel prostheses 334A, 334B, in order to maintain sealing and opposition of the stent with the inner vessel wall. After deployment of branch vessel stent-grafts 334A, 334B, branch delivery catheters 2198A, 2198B and delivery system 1382 are withdrawn from the vasculature.

Figure 25:
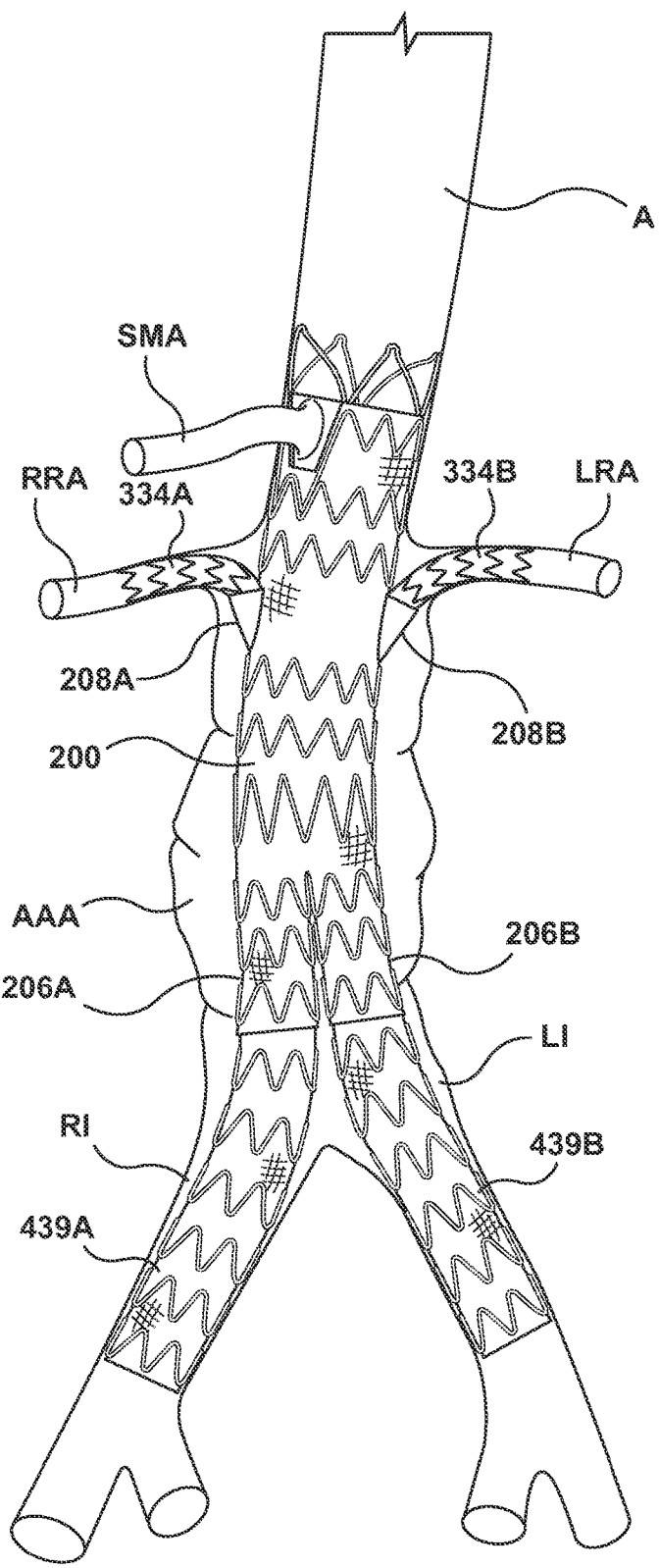

Limb stent-grafts 439A, 439B may be delivered and deployed within legs 206A, 206B of main vessel stent-graft 200, extending into right iliac artery RI and left iliac artery LI, respectively, as shown in FIG. 25. For use in embodiments hereof, limb stent-grafts 439A, 439B are tubes of graft material having self-expanding stent support structures and may be a tubular stent-graft similar to an ENDURANT® type of stent-graft available from Medtronic, Inc. that is delivered and deployed by a delivery system similar to the ENDURANT® stent-graft delivery system also available from Medtronic, Inc. As previously described, legs 206A, 206B of main vessel stent-graft 200 are oriented anterior and posterior within the abdominal aorta. This anterior/posterior orientation allows initial delivery system entry to be the patient's left iliac artery LI or right iliac artery RI without concern over scallop 224 landing on the posterior side. More particularly, access to the abdominal aorta and branches emulating therefrom is typically gained via the femoral artery and the left iliac artery LI or the right iliac artery RI. Cannulating or gaining access to contralateral limb or leg in order to introduce a branch vessel prosthesis often poses challenges, taking a relatively long time, frustrating physicians, requiring additional fluoroscopy time, and possibly resulting in greater blood loss. Often, cannulating the contralateral limb is most difficult when it falls on the posterior side of the aneurysm sac. In main vessel stent-grafts having legs oriented in a medial/lateral configuration, with a scallop oriented anterior to accommodate the SMA, the user is required to deliver the main vessel stent-graft from either the left or right femoral artery but does not have the option of choosing which artery because the ipsilateral limb is standard or pre-determined when assembling the main vessel stent-graft to prevent making custom devices with differing or variable ipsilateral limbs. However, in main vessel stent-graft 200 having legs 206A, 206B oriented in an anterior/posterior configuration, scallop 224 falls anterior regardless of which femoral artery main vessel stent-graft 200 is delivered through and the user has the option of choosing the ipsilateral limb. The posterior leg of main vessel stent-graft 200 is selected to be the ipsilateral limb with main guidewire 1384 running there through, because the contralateral limb is easier to cannulate when it falls on the anterior side of the aneurysm sac. Even in extreme tortuosity causing the graft to torque, the contralateral limb will still always fall on the anterior plane even with up to 90 degrees of angulation along the main vessel stent-graft 200. Accordingly, the anterior/posterior orientation of legs 206A, 206B advantageously facilitates cannulation of the contralateral limb, and wire access is already provided through the posterior limb from the initial stages of the deployment.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A prosthesis for implantation within a blood vessel, the prosthesis comprising:
a tubular body of a graft material;
first and second opposing couplings that extend outwardly from the tubular body, wherein each coupling includes a base coupled to the tubular body, a top spaced from the tubular body, and a coupling lumen disposed between the base and the top that is in fluid communication with a lumen defined by the tubular body; and
a variable stiffness stent coupled to the tubular body proximal of the couplings and including a plurality of crowns and a plurality of struts with each crown being formed between a pair of opposing struts, wherein the variable stiffness stent includes at least two zones of greater flexibility relative to at least two zones of less flexibility, wherein the at least two zones of greater flexibility and the at least two zones of less flexibility comprise a circumference of the variable stiffness stent, and wherein each of the at least two zones of greater flexibility comprise at least two consecutive struts and at least two crowns coupled to the at least two consecutive struts and wherein each of the at least two zones of less flexibility comprises at least two consecutive struts and at least two crowns coupled to the at least two consecutive struts, and wherein one of the at least two zones of greater flexibility is approximately circumferentially aligned with the first coupling and the other of the at least two zones of greater flexibility is approximately circumferentially aligned with the second coupling.

2. The prosthesis of claim 1, wherein the at least two zones of greater flexibility alternate with the at least two zones of less flexibility such that the variable stiffness stent includes four consecutive alternating zones of flexibility including a first zone of a first flexibility, a second zone of second flexibility, a third zone of a third flexibility, and a fourth zone of forth flexibility, wherein the first flexibility and the third flexibility are greater than the second flexibility and the fourth flexibility.

3. The prosthesis of claim 2, wherein struts of the first zone are longer than struts of the second zone.

4. The prosthesis of claim 2, wherein struts of the first zone are thinner than struts of the second zone.

5. The prosthesis of claim 4, wherein struts of the second zone are formed via a series of relatively short tubes slid over a continuous wire.

6. The prosthesis of claim 1, further comprising:
a stent coupled to the tubular body distal to the couplings.

7. The prosthesis of claim 1, wherein each coupling is formed from graft material and includes a support stent coupled thereto.

8. The prosthesis of claim 1, further comprising:
a bifurcated portion having first and second tubular legs coupled to a second end of the tubular body, the legs define lumens that are in fluid communication with a lumen defined by the tubular body, wherein the tubular body is configured for placement within the abdominal aorta and the first and second tubular legs are configured for anterior and posterior placement within the aorta.

9. The prosthesis of claim 1, further comprising:
an anchor stent including a plurality of crowns and a plurality of struts with each crown being formed between a pair of opposing struts, wherein a first proximal-most set of crowns of the anchor stent extend beyond a first edge of the tubular body and a second opposing set of crowns of the anchor stent is coupled to the first edge of the tubular body.

10. The prosthesis of claim 1, further comprising:
a scallop removed from the graft material to extend from a first edge of the tubular body as an open-topped fenestration, wherein the scallop includes first and second opposing side edges and a bottom edge extending there between.

11. The prosthesis of claim 10, wherein the scallop has an oblong shape with the first and second opposing side edges being longer than the bottom edge and the oblong shape is sized to be larger than an ostium of the superior mesenteric artery (SMA).

12. The prosthesis of claim 10, further comprising:
a seal stent coupled to the tubular body adjacent to the first edge thereof and including a plurality of crowns and a plurality of struts with each crown being formed between a pair of opposing struts,
wherein the seal stent includes an integral elongated portion having four consecutive struts including a first long strut extending alongside the first side edge of the scallop and extending distally beyond the bottom edge of the scallop, a first crown connecting the first long strut and a first short strut, the first crown opening towards the scallop such that the first short strut extends from the first crown towards the bottom edge of the scallop, a second crown connecting the first short strut to a second short strut, the second crown opening away from the scallop such that the second short strut extends from the second crown away from the bottom edge of the scallop, and a third crown connecting the second short strut and a second long strut, the third crown opening towards the scallop such that the second long strut extends from the third crown distal of the bottom edge of the scallop towards the first edge of the tubular body alongside the second side edge of the scallop, wherein the first and second long struts are longer than the first and second short struts.

13. The prosthesis of claim 12, wherein the first and second long struts each have a length that is greater than the length of one of the side edges of the scallop and the length of one of the two short struts.

14. The prosthesis of claim 12, wherein the second crown that connects the first and second short struts is positioned at a midpoint of the bottom edge of the scallop.

15. The prosthesis of claim 12, wherein remaining struts of the seal stent other than the four consecutive struts of the integral elongated portion are shorter than the first and second long struts.

16. The prosthesis of claim 15, wherein the remaining struts are equal in length to each other.

17. The prosthesis of claim 12, wherein the first and second long struts are equal in length and the first and second short struts are equal in length.

18. An intraluminal stent device comprising:
a sinusoidal patterned ring of self-expanding material including a plurality of crowns and a plurality of struts with each crown being formed between a pair of opposing struts,
wherein the sinusoidal patterned ring includes four consecutive alternating zones of flexibility including a first zone of a first flexibility, a second zone of second flexibility, a third zone of a third flexibility, and a fourth zone of a fourth flexibility, wherein the first flexibility and the third flexibility are greater than the second flexibility and the fourth flexibility and each zone is approximately ninety degrees of the sinusoidal patterned ring.

19. The prosthesis of claim 18, wherein struts of the first zone are longer than struts of the second zone.

20. The prosthesis of claim 18, wherein struts of the first zone are thinner than struts of the second zone.

\* \* \* \* \*